US000002007B1

(19) United States

(12) Statutory Invention Registration (10) Reg. No.: US H2007 H

Silverman et al. (43) Published: Dec. 4, 2001

(54) INSECTICIDAL N-HETEROCYCLYLALKYL- OR N-[(POLYCYCLYL)ALKYL]-N'SUBSTITUTED PIPERAZINES

(75) Inventors: Ian R. Silverman, Moorestown; Syed F. Ali, Yardville; Daniel H. Cohen, Princeton; John W. Lyga, Basking Ridge, all of NJ (US); Kirk A. Simmons, Newtown, PA (US); Thomas G. Cullen, Milltown, NJ (US)

(73) Assignee: FMC Corporation, Philadelphia, PA (US)

(21) Appl. No.: 08/780,371

(22) Filed: Jan. 9, 1997

Related U.S. Application Data

(60) Provisional application No. 60/010,237, filed on Jan. 19, 1996.

(51) Int. Cl.[7] ..... C07D 295/00; C07D 403/00; C07D 241/04; C07D 241/02

(52) U.S. Cl. ..... 544/358; 544/359; 544/363; 544/366; 544/369; 544/372; 544/373; 544/376; 544/391; 544/398; 544/402; 544/410

(58) Field of Search ..... 544/358, 359, 544/363, 366, 369, 372, 373, 376, 391, 398, 402, 410

(56) References Cited

U.S. PATENT DOCUMENTS

| | | | | |
|---|---|---|---|---|
| 3,362,956 | * | 1/1968 | Archer | 260/268 |
| 3,920,442 | | 11/1975 | Albert et al. | 71/92 |
| 4,179,505 | | 12/1979 | Raeymaekers et al. | 424/250 |
| 4,935,426 | * | 6/1990 | Zipplies et al. | 514/255 |
| 5,166,205 | | 11/1992 | Cuberes-Altisent et al. | 514/252 |
| 5,418,237 | | 5/1995 | Böttcher et al. | 514/253 |

FOREIGN PATENT DOCUMENTS

| | | |
|---|---|---|
| 0 496 692 A1 | 7/1992 | (EP) . |
| 944 443 | 12/1963 | (GB) . |

OTHER PUBLICATIONS

"Benzylpiperazine Derivatives, V. Quantitative Structure–Activity Relationships of 1–Benzyl–4–diphenylmethylpiperazine Derivatives for Cerebral Vasodilating Activity," H. Ohtaka et al., *Chem. Pharm. Bull.*, vol. 35(10), 1987, pp. 4117–4123.*

"σ Ligands with Subnanomolar Affinity and Preference for the $\sigma_2$ Binding Site. 1. 3–(ω–Aminoalkyl)–1H–Indoles," Perregaard et al., *J. Med. Chem.*, 1995, 38, pp. 1998–2008.*

Venero et al., "Process for the preparation of nes (diphenylmethyl)piperazine derivatives as antihistaminics and antiallergics", *Chem. Abstr.*, 1993, 118 (5), Abstract No. 38948h.

Ohtaka et al., "Benzylpiperazine Derivatives. VI. Design and Syntheses of Vinylogs of 1–Benzyl–4–diphenylmethylpiperazine Derivatives and Their Cerebral Vasodilating Activities", *Chem. Pharm. Bull.*, 1987, 35(10), 4124–4129.

Ohtaka et al., "Benzylpiperazine Derivatives. IV. Syntheses and Cerebral Vasodilating Activities of 1–Benzyl–4–diphenylmethyl–piperazine Derivatives", *Chem. Pharm. Bull.*, 1987, 35(8), 3270–3275.

* cited by examiner

*Primary Examiner*—Peter M. Poon
*Assistant Examiner*—Aileen J. Baker
(74) *Attorney, Agent, or Firm*—Donald J. Silvert; I. Robert Silverman; H. Robinson Ertelt

(57) ABSTRACT

Compounds of the following structure are disclosed as effective insecticides:

in which: A and B are independently lower alkyl; U is lower alkylidene, lower alkenylidene, or CH—Z, where Z is hydrogen, lower alkyl, lower cycloalkyl, or phenyl; R is phenyl or a dibenzocyclo($C_{5-8}$)alkyl, each optionally substituted, or where $R^3$ and $R^4$ are independently selected from phenyl, optionally substituted with, halogen, lower alkyl, lower haloalkyl, lower alkoxy, lower haloalkoxy, lower alkenyl, or phenyl; $R^1$ is selected from a variety of substituents, including 3-$R^2$, where $R^2$ is where D, E, and G are hydrogen, hydroxy, halogen, cyano, hydroxy, lower alkyl, lower haloalkyl, lower alkoxy, nitro, lower haloalkylsuffonyloxy, lower alkylcarboxylato, lower alkylcarbonylamino, lower alkylcarbonyl, lower alkoxycarbonyl, arylcarbonylamino; D and E taken together may form the group —O($CH_2$)O—; J is hydrogen or lower alkyl; m is 2 or 3, n is 1, 2, or 3; and halogen is chlorine, bromine, or fluorine.

49 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

INSECTICIDAL N-HETEROCYCLYLALKYL- OR N-[(POLYCYCLYL)ALKYL]-N'SUBSTITUTED PIPERAZINES

This application claims benefit of Provisional No. 60/010,237 filed Jan. 19, 1996.

The present invention relates to methods for controlling insects. In particular, it relates to control by application of certain N-heterocyclylalkyl- or N-[(polycyclyl)alkyl]N'-substituted piperazine derivatives to locus where insect control is needed. While not all compounds of the class are novel, the use of the compounds of the invention as insecticides is heretofore unknown.

It has now been found that compounds of the following structure and their agriculturally acceptable salts are active as insecticides:

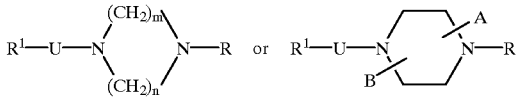

where:

A and B are independently selected from lower alkyl;

U is selected from lower alkyl, lower alkenyl, CH—Z, where Z is independently selected from hydrogen, lower alkyl, lower cycloalkyl, and phenyl;

R is selected from phenyl, optionally substituted with halogen, lower alkyl, lower alkoxy, phenyl, or phenoxy, and from polycyclyl, optionally substituted with halogen, lower alkyl, or lower alkoxy, where polycyclyl is a dibenzocyclo($C_{5-8}$)alkyl; and

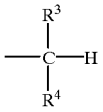

where $R^3$ and $R^4$ are independently selected from phenyl, optionally substituted with halogen, lower alky, lower haloalkyl, lower alkoxy, lower haloalkoxy, lower alkenyl, or phenyl;

$R^1$ is phenyl, naphthyl, tetrazolylphenyl, phenylcyclopropyl, phenoxyphenyl, benzyloxyphenyl, pyridylphenyl, pyridyloxyphenyl, thiadiazolyloxyphenyl, benzothienyl, benzimidazolyl, indolyl, pyrrolyl, or quinolyl, each optionally substituted with halogen, cyano, hydroxy, lower alkyl, lower haloalkyl, lower alkoxy, amino, lower dialkylamino, nitro, lower haloalkylsulfonyloxy, lower alkylcarbonyloxy, lower alkylcarbonylamino, lower alkoxycarbonyl, lower alkoxyalkoxycarbonyl, lower cycloalkylalkoxycarbonyl, lower alkoxyalkylalkoxycarbonyl, lower alkoxycarbonylamino, alkoxythiocarbonylamino, lower alkyldithiocarbonylamino, lower dialkyldioxolylalkoxycarbonylamino, or halophenylamino; or lower alkyl substituted with any one of the foregoing cyclic $R^1$ groups; or 3-$R^2$, where $R^2$ is

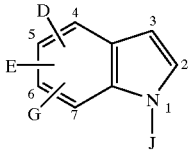

where D, E, and G are independently selected from hydrogen, halogen, cyano, hydroxy, lower alkyl, lower haloalkyl, lower alkoxy, nitro, lower haloalkylsulfonyloxy, lower alkylcarbonyloxy, lower alkylcarbonylamino, arylcarbonylamino, lower alkylcarbonyl, lower alkoxycarbonyl, or D and E taken together may form the group —O($CH_2$)O—, and J is hydrogen or lower alkyl;

m is 2 or 3 and n is 1, 2, or 3; and halogen is chlorine, fluorine, or bromine, lower means having from 1 to 6 carbon atoms and any aliphatic chain of three or more carbons may be straight or branched.

Preferred compounds are those in which

U is $CH_2$;

R is

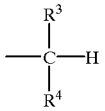

where $R^3$ and $R^4$ are independently selected from chlorophenyl, fluorophenyl, methylphenyl, trifluoromethylphenyl, methoxyphenyl, and trifluoromethoxyphenyl;

$R^1$ is phenyl, tetrazolylphenyl, pyridylphenyl, pyridyloxyphenyl; each optionally substituted with halogen, cyano, hydroxy, lower alkyl, lower haloalkyl, lower alkoxy, amino, lower dialkylamino, lower alkylcarbonyloxy, lower alkylcarbonylamino, lower alkoxycarbonyl, lower alkoxyalkoxycarbonyl, lower cycloalkylalkoxycarbonyl, lower alkoxyalkylalkoxycarbonyl, or lower alkoxycarbonylamino; or lower alkyl substituted with any one of the foregoing cyclic $R^1$ groups; or 3-$R^2$, where $R^2$ is

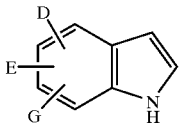

where D is hydrogen, hydroxy, chloro, fluoro, methyl, methoxy, or phenylcarbonylamino; E and G are independently selected from hydrogen, chloro, fluoro, methyl, and methoxy, with the proviso that when $R^1$ is lower dialkylaminophenyl, $R^3$ and $R^4$ are each trifluoromethoxyphenyl;

m and n are 2; and halogen is chlorine or fluorine, for aliphatic groups lower means having from 1 to 3 carbon atoms and for alicyclic groups lower means having 3 to 6 carbons.

Particularly preferred are those compounds in which

U is $CH_2$;

R is

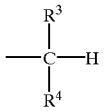

where $R^3$ and $R^4$ are independently selected from 4-chlorophenyl, 4-fluorophenyl, 4-methylphenyl, 4-trifluoromethylphenyl, and 4-trifluoromethoxyphenyl;

$R^1$ is phenyl substituted in the 4-position with lower dialkylamino, lower alkoxycarbonylamino, tetrazolyl, pyridyl, or pyridyloxy; each tetrazolyl or pyridyl group optionally substituted with halogen, cyano, lower alkyl, lower haloalkyl, or lower alkoxy; or 3-$R^2$, where $R^2$ is

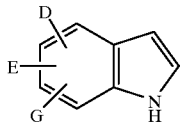

where D is hydrogen, 4-chloro, 4-fluoro, 4-hydroxy, or 4-phenylcarbonylamino; E is hydrogen, 5-chloro, 5-methyl, or 6-fluoro; G is hydrogen or 5-methoxy;

m and n are 2; and halogen is chlorine or fluorine, for aliphatic groups lower means having from 1 to 3 carbon atoms and for alicyclic groups lower means having 3 to 6 carbons.

The N-heterocyclylalkyl- or N-[(polycyclyl)alkyl]-N'-substituted piperazine derivatives of the present invention were prepared by methods known to one skilled in the art. A number of synthesis routes were employed in obtaining the targeted compounds.

Synthesis of the piperazine starting materials are depicted in Schema 1. Various R group intermediates were prepared by first reacting an aryl Grignard reagent (A) with a substituted aldehyde (B), for example, 2,4-dichlorobenzaldehyde, to afford the corresponding (substituted diaryl)methanol (C), for example, (2-chlorophenyl)(4-chlorophenyl)methanol. C can also be prepared by reacting substituted benzophenones (D) with sodium borohydride. The diaryl methanol (C) is then treated with thionyl chloride affording a (substituted diaryl)methyl chloride (E), for example, (2-chlorophenyl)(4-chlorophenyl)methyl chloride. The so-prepared diaryl methyl chloride (E) can then be reacted with piperazine to form the N-[(substituted diaryl)methyl]piperazine (F). The piperazine (F) can be reacted with an appropriate halide (G), affording the targeted N-(substituted alkyl)-N'-[(substituted diaryl)methyl]piperazine (H), for example, N-(4-chloroindol-3-yl-methyl)-N'-[(4-chlorophenyl)(2-chlorophenyl)methyl)piperazine. Alternatively, a substituted indole (I) capable of undergoing a Mannich-type reaction is condensed with formaldehyde and the N-substituted piperazine in dioxane and acetic acid to afford the targeted N-(substituted alkyl)-N'-(R-substituted)-piperazine (J), for example, N-(benzo[β]ythien-3-ylmethyl)-N'-[bis(4-chlorophenyl)methyl]piperazine. Example 1 provides the detailed procedure for this route.

As depicted by Schema 2, those compounds in which Z is other than hydrogen are prepared by first reacting a substituted indole (I) with phosphorus oxychloride and N,N-dimethylformamide, affording the corresponding substituted aldehyde (K). K is in turn condensed with N-[(substituted diaryl)-methyl]piperazine (F) to form the imine and then reacted with the appropriate alkyl or aryl magnesium halide, for example, phenyl magnesium chloride, affording the targeted N-[(alkyl)(substituted indole)alkyl]- or N-[(aryl)(substituted heterocyclyl)alkyl]-N'-[(substituted diaryl)methyl]piperazine (L), for example, N-[(phenyl)(4-chloroindol-3-yl)methyl]-N'-[bis(4-chlorophenyl)-methyl]piperazine. The substituted indole (I) can also be reacted with an aldehyde and N-[(substituted diaryl)methyl]piperazine (F) under acidic conditions, affording the targeted N-[(alkyl)(substituted heterocyclyl)alkyl]- or N-[(aryl)(substituted heterocyclyl)alkyl]-N'-[(substituted diaryl)methyl]piperazine (L). Examples 2 and 4 provide detailed procedures for this route.

Compounds having the F structure are particularly useful intermediates. The compound with $R^3$ and $R^4$ each trifluoromethoxyphenyl, i.e., N-[bis(4-trifluoromethoxyphenyl)methyl]piperazine, is thought to be novel and has the following NMR spectrum, proton assignment in ppm in $CDCl_3$: 2.41 (m, 4H); 2.54 (d of m, 2H); 2.98 (m, 2H); 3.39 (t, 1H); 7.15 (d, 4H); 7.40 (d 4H).

At this point an N-[(substituted diaryl)methyl]piperazine (F) can be reacted with an appropriately substituted aldehyde for example, 4-dimethylaminobenzaldehyde, under acidic conditions and at 100 ° C., affords the targeted N-(substituted alkyl)-N'-[(substituted diaryl)methyl] piperazine (M). Example 5 provides the detailed procedure for this route.

Schema 3 outlines routes to compounds where the tether U is varied. An acid chloride (N) is derivatized with an appropriate N-[(substituted diaryl)-methyl]piperazine (E), affording the targeted N-[(substituted)alkylcarbonyl]-N'-[(substituted diaryl)methyl]piperazine (O). The piperazine (O) can also be prepared by derivatizing a substituted carboxylic acid (P), for example, 2-methyl-3-indoleacetic acid, with an appropriate N-[(substituted diaryl)methyl]-piperazine (F). The piperazine (O) is then converted to the targeted N-(substituted alkyl)-N'-[(substituted diaryl) methyl]piperazine (J), for example, N-[2-(2-methylindol-3-yl)ethyl]-N'-[bis(4fluorophenyl)methyl]piperazine. Example 6 provides the detailed procedure for this route.

To obtain compounds in which U is a lower alkenyl, a cinnamic acid (Q) may be reacted with lithium aluminum hydride and thionyl chloride, as previously described, to form a substituted allyl chloride (S). The allyl chloride (S) is then reacted with the appropriate N-[bis(substituted) methyl]-piperazine (F) under basic conditions to form the targeted N-[(substituted)-alkenyl]-N'-[bis(substituted) methyl]piperazine (T). Example 3 provides the detailed procedure for this route.

Schema 1

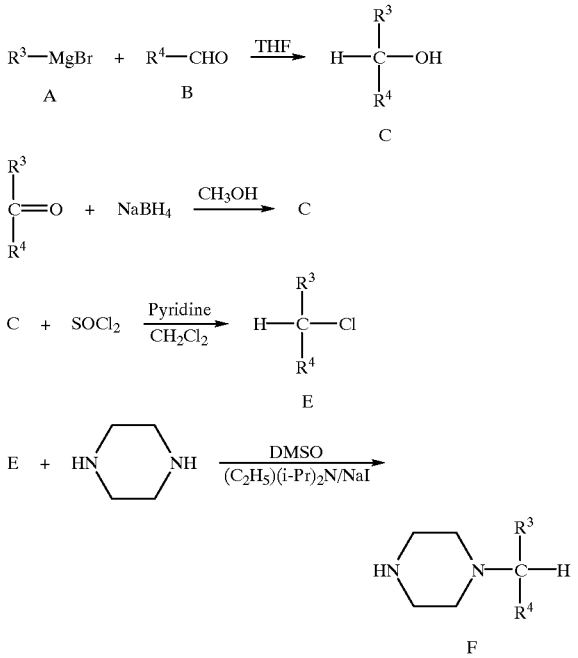

-continued

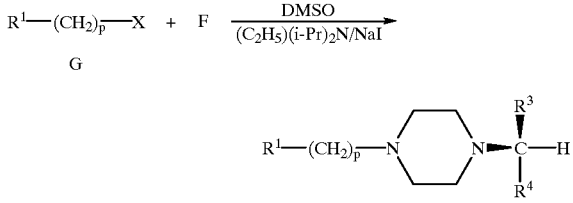

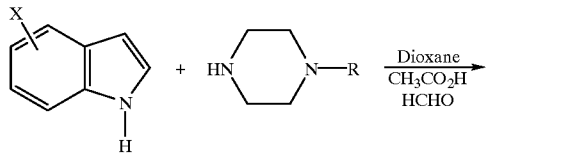

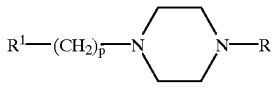

J where $R^1$ is heterocyclyl

Schema 2

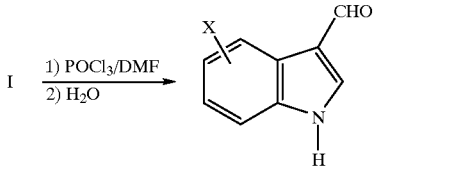

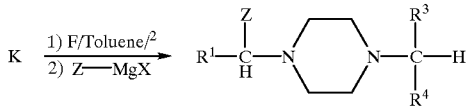

L where $R^1$ is a substituted indole

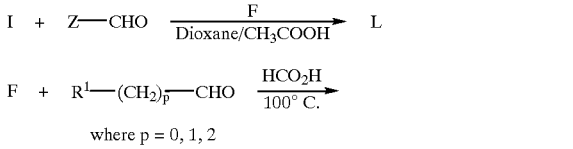

where p = 0, 1, 2

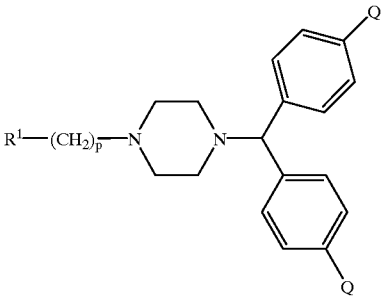

M

Schema 3

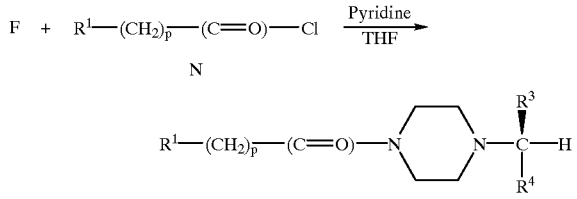

Free piperazine or the HCl salt

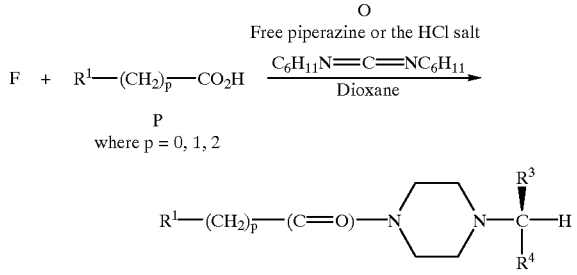

where p = 0, 1, 2

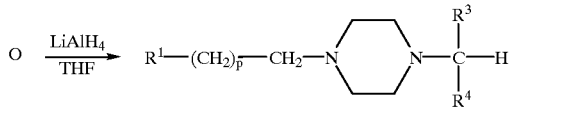

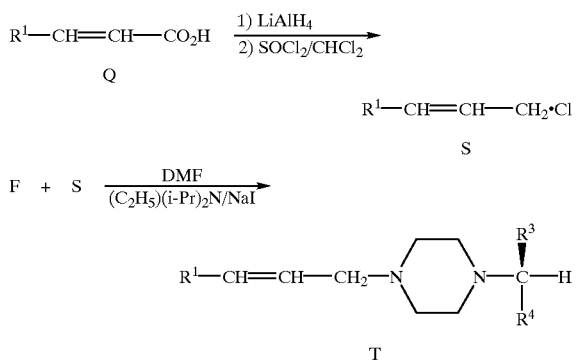

EXAMPLE 1

Synthesis of N-(4-Chloroindol-3-ylmethyl)-N'-[(4-Chlorophenyl)(2-Chlorophenyl)Methyl]-Piperazine (Compound 19)

Step A Synthesis of (2-chlorophenyl)(4-chlorophenyl) methanol as an intermediate Under a nitrogen atmosphere, 1.7 grams ( 0.044 mole) of sodium borohydride pellets was added to 100 ml of stirred ethanol. To this was added 10.0 grams (0.040 moles) of 2,4'-dichlorobenzophenone in one portion. Upon completion of the addition the reaction mixture was stirred at ambient temperature for about 18 hours. After this time the ethanol was removed under reduced pressure, and the resulting residue was taken up in 250 mL of aqueous 5% sodium hydroxide solution. The solution was extracted with two 100 mL portions of diethyl ether. The combined ether extracts were washed with aqueous saturated sodium chloride solution. The organic layer was filtered and the filtrate concentrated under reduced pressure, yielding 9.5 grams of (2-chlorophenyl)(4-chlorophenyl)methanol. The NMR spectrum was consistent with the proposed structure.

Step B Synthesis of (2-chlorophenyl)(4-chlorophenyl) methyl chloride as an intermediate A stirred solution of 9.0 grams (0.036 mole) of (2-chlorophenyl)(4-chlorophenyl)methanol in 90 mL of chloroform was cooled to 0° C., and 5.3 mL (0.072 mole) of thionyl chloride was added. Upon completion of the addition the reaction mixture was allowed to warm to ambient temperature, where it stirred for about 18 hours. After this time the reaction mixture was filtered and concentrated under reduced pressure. The filtrate was taken up in hexane and subjected to column chromatography on silica gel with hexane as eluant. The product-containing fractions were combined and concentrated under reduced pressure, yielding 10.0 grams of (2-chlorophenyl)(4-chlorophenyl)methyl chloride. The NMR spectrum was consistent with the proposed structure.

Step C Synthesis of N-(ethoxycarbonyl)-N'-[(2-chlorophenyl)(4-chloro phenyl)methyl]piperazine as an intermediate A stirred solution of 2.5 grams (0.009 mole) of (2-chlorophenyl)(4-chlorophenyl)methyl chloride, 1.6 grams (0.010 mole) of ethyl 1-piperazine-carboxylate, 1.4 mL (0.010 mole) of triethylamine, and 1.2 grams (0.008 mole) of sodium iodide in 25 mL of toluene was heated at reflux for about 18 hours. The resulting precipitate was collected by filtration. The filtrate was cooled to ambient temperature and 200 mL of aqueous saturated sodium bicarbonate solution was added to it. The mixture was extracted with two 100 mL portions of ethyl acetate. The combined ethyl acetate layers were washed with two 25 mL portions of an aqueous saturated sodium chloride solution. The organic layer was dried with sodium sulfate and concentrated under reduced pressure, yielding 3.2 grams of crude material. The crude material was subjected to column chromatography on silica gel with 50-25% hexane in methylene chloride, followed by pure methylene chloride, as eluants. The product-containing fractions were combined and concentrated under reduced pressure, yielding 1.0 gram of N-(ethoxycarbonyl)-N'-[(2-chlorophenyl)(4-chlorophenyl) methyl]piperazine. The NMR spectrum was consistent with the proposed structure.

Step D Synthesis of N'-[(2-chlorophenyl)(4-chlorophenyl) methyl]piperazine as an intermediate To a stirred solution of 0.9 gram (0.002 mole) of N-(ethoxycarbonyl)-N'-[(2-chlorophenyl)(4-chlorophenyl) methyl]piperazine in 10 mL of tetrahydrofuran was added 10 mL of methanol and 10 mL of aqueous 50% sodium hydroxide. Upon completion of the addition the reaction mixture was warmed to 80° C., where it stirred for 24 hours. At the end of this time the reaction mixture was concentrated under reduced pressure. The concentrate was dissolved in chloroform, and the solution was stirred for 40 minutes. The resulting precipitate was collected by filtration. The filtrate was concentrated under reduced pressure, yielding 0.6 gram of crude material. The crude material was purified by preparative thin layer chromatography (TLC). Elution was accomplished with 1:1 acetone: methanol. The product-containing fractions were combined and concentrated under reduced pressure, yielding 0.4 gram of N'-[(2-chlorophenyl) (4-chlorophenyl)-methyl]piperazine. The NMR spectrum was consistent with the proposed structure.

Step E Synthesis of N-(4-chloroindol-3-ylmethyl)-N'-[(4-chlorophenyl) (2-chlorophenyl)methyl]piperazine (Compound 19)

A stirred solution of 0.4 gram (0.001 mole) of N'-[(2-chlorophenyl)(4-chlorophenyl)methyl]piperazine in 1 mL of dioxane was cooled to 0° C. To this was added 2 mL of glacial acetic acid followed by 0.14 mL of 37% aqueous formaldehyde. A solution of 0.2 gram (0.001 mole) of 4-chloroindole in 1 mL of dioxane was then slowly added. Upon completion of the addition the reaction mixture was warmed to ambient temperature where it stirred for five hours. The reaction mixture was then cooled to 0° C., neutralized with aqueous saturated sodium bicarbonate solution, and extracted with two portions of diethyl ether. The combined extracts were washed with an aqueous saturated sodium chloride solution and dried with sodium sulfate, yielding 0.6 gram of crude material. The crude material was purified by preparative TLC. Elution was accomplished with 3:2 ethyl acetate: methylene chloride. The product-containing fractions were combined and concentrated under reduced pressure, yielding 0.4 gram of N-(4-chloroindol-3-ylmethyl)-N'-[(4-chlorophenyl)(2-chlorophenyl)methyl]piperazine. The NMR spectrum was consistent with the proposed structure.

EXAMPLE 2

Synthesis of N-[(Phenyl)(4-Chloroindol-3-yl) Methyl]-N'-[bis(4-Chlorophenyl)Methyl]Piperazine (Compound 59)

Step A Synthesis of 4-chloro-3-formylindole as an intermediate

During a period of five minutes 2.3 grams (0.015 mole) of phosphorus oxychloride was added dropwise to 10 mL of N,N-dimethylformamide. The solution was stirred for 30 minutes and then cooled in an ice bath. To this was added dropwise a solution of 2.0 grams (0.013 mole) of 4-chloroindole in 3 mL of N,N-dimethylformamide. Upon completion of the addition the ice bath was removed, and the reaction mixture was warmed to ambient tempeature, where it stirred for 1.5 hours. After this time the reaction mixture was warmed to 40° C., where it was stirred for 30 minutes, and then poured onto 50 grams of ice. A solution of 5.9 grams (0.146 mole) of sodium hydroxide in 20 mL of water was added during a 2–3 minute period, after which the mixture was heated to reflux and then cooled to ambient temperature. The cooled mixture was poured into 500 mL of water, stirred at ambient temperature for about 18 hours, and then filtered to collect a solid that had precipitated. The solid was washed with three portions of water and then dissolved in ethyl acetate. The ethyl acetate solution was subjected to column chromatography on silica gel with 1:1 ethyl acetate: hexane as eluant. The product-containing fractions were combined and concentrated under reduced pressure, yielding 1.4 grams of 4-chloro-3-formylindole. The NMR spectrum was consistent with the proposed structure.

Step B Synthesis of N-(4-chloro-3H-indol-3-ylmethylenyl)-N'-[bis(4-chlorophenyl)methyl]piperazine as an intermediate A stirred solution of 0.2 gram (0.001 mole) of 4-chloro-2-formylindole and 0.4 gram (0.001 mole) of N'-[bis(4-chlorophenyl)methyl]piperazine in 75 mL of toluene was heated at reflux for 16 hours using a Dean Stark trap. After this time the heat was removed, and the reaction mixture was concentrated under reduced pressure, yielding about 0.6 gram of solid N-(4-chloro-3H-indol-3-ylmethenyl)-N'-[bis (4-chlorophenyl)methyl]piperazine.

Step C Synthesis of N-[(phenyl)(4chloroindol-3-yl)methyl]-N'-[bis(4-chlorophenyl)methyl]piperazine (Compound 59)

A mixture of about 0.6 gram (0.001 mole) of N-(4-chloro-3H-indol-3-yl-methinyl)-N'-[bis(4-chlorophenyl)methyl] piperazine in 20 mL of tetrahydrofuran was stirred at ambient temperature, and 1.2 mL (0.002 mole) of 2M phenyl magnesium chloride (in tetrahydrofuran) was added dropwise during a 5 minute period. Upon completion of the addition the reaction mixture was stirred for 30 minutes at ambient temperature, then heated to 50–80° C., where it stirred for two hours. After this time the homogeneous reaction mixture was cooled to ambient temperature and poured into 200 mL of an aqueous saturated ammonium chloride solution. The resulting solution was then extracted with three 100 mL portions of ethyl acetate. The combined extracts were washed with two 100 mL portions of aqueous sodium chloride solution, dried with sodium sulfate, and filtered. The filtrate was concentrated under reduced pressure to a residue, which was subjected to column chromatography on silica gel. Elution was accomplished with 7:13 ethyl acetate:hexane. The product-containing fractions were combined and concentrated under reduced pressure, yielding 0.3 gram of N-[(phenyl)(4-chloroindol-3yl)methyl]-N'-[bis(4-chlorophenyl)methyl]piperazine, mp 100–105° C. The NMR spectrum was consistent with the proposed structure.

EXAMPLE 3

Synthesis of N-[3-(4-Nitrophenyl)-2-Propenyl]-N'-[bis(4-Fluorophenyl)Methyl]Piperazine (Compound 108)

A solution of 0.5 gram (0.002 mole) of 3-(4-nitrophenyl)-2-propenyl chloride in 5 mL of dimethyl sulfoxide was added to a solution of 0.7 gram (0.002 mole) of N-[bis(4-fluorophenyl)methyl]piperazine in 10 mL of dimethyl sulfoxide. To this was added 0.1 gram (0.0005 mole) of sodium iodide as a catalyst. Upon completion of the addition 1.2 grams (0.010 mole) of N,N-diisopropylethylamine was added dropwise. To effect solution the reaction mixture was then warmed to 50–80° C., where it stirred for four hours. After this time the reaction mixture was cooled to ambient temperature, where it stirred for about 18 hours. The reaction mixture was then poured into 50 mL of aqueous saturated sodium bicarbonate solution and then extracted with three 50 mL portions of diethyl ether. The combined extracts were washed with 75 mL of aqueous saturated sodium chloride solution, dried over magnesium sulfate, and filtered. The filtrate was concentrated under reduced pressure, yielding a crude oil, which was subjected to column chromatography on silica gel. Elution was accomplished with 1:1 ethyl acetate:heptane. The product-containing fractions were combined and concentrated under reduced pressure, yielding 0.5 gram of of N-[3-(4-nitrophenyl)-2-propenyl]-N'-[bis(4-fluorophenyl)methyl]piperazine. The NMR spectrum was consistent with the proposed structure.

EXAMPLE 4

Synthesis of N-[1-(Indol3-yl)Propyl]-N'-[(4-Chlorophenyl) (Phenyl)Methyl]Piperazine (Compound 54)

A solution of 2.0 grams (0.006 mole) of N-[(4-chlorophenyl)(phenyl)-methyl]piperazine and 0.5 mL (0.007 mole) of propionaldehyde in 8.0 mL of dioxane and 8.0 mL of glacial acetic acid was stirred and cooled in an ice bath. To this a solution of 0.7 gram (0.006 mole) of indole in 10.0 mL of dioxane was added dropwise during a 15 minute period. Upon completion of the addition the reaction mixture was allowed to warm to ambient temperature, where it stirred for about 18 hours, after which the reaction mixture was poured into a mixture of diethyl ether and aqueous 5% sodium hydroxide. The ether layer was separated and washed with water and then with an aqueous saturated sodium chloride solution. The organic layer was dried with magnesium sulfate and filtered. The filtrate was concentrated under reduced pressure to an oil, which was subjected to column chromatography on silica gel. Elution was accomplished with pure hexane, followed by diethyl ether/hexane mixtures and then pure diethyl ether. The product-containing fractions were combined and concentrated under reduced pressure, yielding 0.3 gram of N-[1-(indol-3yl)propyl]-N'-[(4chlorophenyl)-(phenyl)methyl]piperazine. The NMR spectrum was consistent with the proposed structure.

EXAMPLE 5

Synthesis of N-(4-Dimethylaminophenylmethyl)-N'-[bis(4-Cyanophenyl)Methyl]Piperazine (Compound 118)

Step A Synthesis of N-t-butyl-4-bromobenzamide as an intermediate

Under a nitrogen atmosphere, 4.5 mL (0.043 mole) of t-butylamine was added to a solution of 7.7 grams (0.035 mole) of 4-bromobenzoyl chloride in 75 mL of tetrahydrofuran. To this was added dropwise 6.7 mL (0.048 mole) of triethylamine. Upon completion of the addition the reaction mixture was stirred at ambient temperature for about 18 hours, after which it was poured into 50 mL of water, and the organic layer was separated. The aqueous layer was extracted with one 50 mL portion of diethyl ether. The combined organic layer and extract were washed with two 25 mL portions of water, dried with sodium sulfate, and filtered. The filtrate was concentrated under reduced pressure, yielding 8.4 grams of N-t-butyl-4-bromobenzamide, mp 126–128° C. The NMR spectrum was consistent with the proposed structure.

Step B Synthesis of bis[4-(t-butylaminocarbonyl)phenyl] methanol as an intermediate Under a nitrogen atmosphere, a stirred solution of 7.8 grams ( 0.030 mole) of N-t-butyl-4-bromobenzamide in 125 mL of tetrahydrofuran was cooled to −60° C., and 28 mL (0.063 mole) of 2M n-butyllithium in hexanes was added dropwise during a 30 minute period. Upon completion of the addition the reaction mixture was stirred at −60° C. for 1.5 hours, then a solution of 1.2 mL (0.015 mole) of ethyl formate in 25 mL of diethyl ether was added dropwise. The reaction mixture was stirred at −60° C. for an additional 1.5 hours, and 150 mL of aqueous saturated ammonium chloride solution was added dropwise, followed by 50 mL of methylene chloride and 50 mL of ethyl acetate, and then the mixture was warmed to ambient temperature. The organic layer was separated and washed with one 50 mL portion of water and one 50 mL portion of an aqueous saturated sodium chloride solution. The organic layer was dried with sodium sulfate and filtered. The filtrate was concentrated under reduced pressure, yielding 2.9 grams. The NMR spectrum was consistent with the proposed structure.

Step C Synthesis of bis(4-cyanophenyl)methyl chloride as an intermediate

Under a nitrogen atmosphere, a stirred solution of 2.9 grams (0.008 mole) of bis[4-(t-butylaminocarbonyl)phenyl] methanol in 25 mL (0.0340 mole) of thionyl chloride was heated at reflux for five hours. After this time the reaction mixture was concentrated under reduced pressure, yielding a residue. The residue was dissolved in about 10 mL of toluene. The solution was again concentrated under reduced pressure, yielding a residue. This residue was again dissolved in about 10 mL of toluene, and the resulting solution was concentrated under reduced pressure, yielding 2.2 grams of a brown liquid. Methylene chloride was added to 1.0 gram of the liquid, and the resulting solution was filtered through a silica gel pad. The filtrate was washed with methylene chloride. The filtrate and wash were combined and concentrated under reduced pressure, yielding 0.7 gram of bis(4-cyano-phenyl)methyl chloride. The NMR spectrum was consistent with the proposed structure.

Step D Synthesis of N'-[bis(4-cyanophenyl)methyl] piperazine as an intermediate

This compound was prepared in the manner of Example 3, with 0.63 gram (0.002 mole) of bis(4-cyanophenyl) methyl chloride, 0.86 gram (0.010 mole) of piperazine, and 1.4 mL (0.010 mole) of triethylamine in 20 mL of dimethyl sulfoxide as reagents and 0.1 gram (0.0005 mole) of sodium iodide as catalyst. This procedure differed in that triethylamine was used, rather the N,N-diisopropylethylamine, and the reaction mixture was stirred at ambient temperature for about 48 hours rather than at 50–60° C. for about 18 hours. The yield of N'-[bis(4-cyanophenyl)methyl]piperazine was 0.4 gram. The NMR spectrum was consistent with the proposed structure.

Step E Synthesis of N-(4-dimethylaminophenylmethyl)-N'-[bis(4-cyanophenyl)methyl]piperazine (Compound 118)

A stirred solution of 0.4 gram (0.002 mole) of N-[bis(4-cyanophenyl)-methyl]piperazine and 0.2 gram (0.002 mole) of 4-dimethylaminobenzaldehyde was heated in an oil bath to 100° C., and then 0.1 mL (0.002 mole) of formic acid was added. Upon completion of the addition the reaction mixture was stirred at 100° C. for five hours, after which time it was cooled to ambient temperature, where it was stirred for about 18 hours. At the conclusion of this period 25 mL of methylene chloride was added to the reaction mixture, and the solution was extracted with two 20 mL portions of aqueous 10% hydrochloric acid. The hydrochloric acid extracts were made basic with solid sodium bicarbonate and then extracted with two 25 mL portions of methylene chloride. The combined extracts were washed with one 25 mL portion of water, dried with sodium sulfate, and filtered. The filtrate was concentrated under reduced pressure, yielding 0.4 gram of a brown liquid, which was subjected to column chromatography on silica gel. Elution was accomplished with pure methylene chloride, followed by 1:9 diethyl ether:methylene chloride. The product-containing fractions were combined and concentrated under reduced pressure, yielding 0.2 gram of a white solid. The white solid was purified by column chromatography on alumina with diethyl ether as the eluant. The product-containing fractions were combined and concentrated under reduced pressure, yielding 0.1 gram of N-(4-dimethylaminophenylmethyl)-N'-[bis(4-cyanophenyl) methyl]piperazine. The NMR spectrum was consistent with the proposed structure.

EXAMPLE 6

Synthesis of N-(2-Methylindol-3-ylethyl)-N'-[bis(4-Fluorophenyl)Methyl]Piperazine (Compound 36)

Step A Synthesis of 2-methylindol-3-ylacetyl chloride as an intermediate

N,N-dimethylformamide, 2 drops, was added to a stirred mixture of 5.0 grams (0.026 mole) of 2-methylindole-3-acetic acid in 125 mL of diethyl ether. The solution was then cooled to 0° C., and 2.5 mL (0.029 mole) of oxalyl chloride was slowly added. Upon completion of the addition the reaction mixture was warmed to ambient temperature during 30 minutes, where it stirred for 1.5 hours, after which the reaction mixture was concentrated under reduced pressure to a residue. The residue was taken up in 30 mL of tetrahydrofuran and then divided into two 15 mL portions. Each 15 mL portion contained about 0.013 mole of 2-methylindol-3-ylacetyl chloride.

Step B Synthesis of N-(2-methylindol-3-ylacetyl)-N'-[bis(4-fluoro phenyl)methyl]piperazine as an intermediate Under a nitrogen atmosphere a 15 mL solution of 2-methylindol-3-ylacetyl chloride (0.013 mole) in tetrahydrofuran was added to a stirred solution of 3.9 grams (0.014 mole) of N-[bis(4-fluorophenyl)methyl]piperazine and 1.1 mL (0.013 mole) of pyridine in 50 mL of dried tetrahydrofuran. Upon completion of the addition the reaction mixture was stirred at ambient temperature for about 18 hours, after which the reaction mixture was poured into a mixture of 200 mL of ethyl acetate and 100 mL of aqueous saturated sodium bicarbonate solution. The organic layer was separated and washed with one portion of a saturated sodium chloride solution, dried with sodium sulfate, and filtered. The filtrate was concentrated under reduced pressure to a solid, which was taken up in hexane. This solution was concentrated under reduced pressure, yielding 3.2 grams of N-(2-methylindol-3-ylacetyl)-N'-[bis(4-fluorophenyl)methyl] piperazine, mp 93–103° C. The NMR spectrum was consistent with the proposed structure.

Step C Synthesis of N-(2-methylindol-3-ylethyl)-N'-[bis(4-fluoro phenyl)methyl]piperazine (Compound 36)

A solution of 1.5 grams (0.003 mole) of N-(2-methylindol-3-ylacetyl)-N'-[bis(4-fluorophenyl)methyl] piperazine in 10.0 mL of anhydrous tetrahydrofuran was added to a stirred mixture of 0.4 gram (0.010 mole) of lithium aluminum hydride in 5.0 mL of anhydrous tetrahydrofuran. Upon completion of the addition the reaction mixture was heated to reflux, where it stirred for 2.5 hours. The reaction mixture was cooled to 0° C., and water was added, followed by 50 mL of aqueous 10% sodium hydroxide. The solution was warmed to ambient temperature and then extracted with ethyl acetate. The extract was dried with sodium sulfate and filtered. The filtrate was concentrated under reduced pressure, yielding 0.7 gram of N-(2-methylindol-3-ylethyl)-N'-[bis(4-fluorophenyl)methyl] piperazine, mp 65–73° C. The NMR spectrum was consistent with the proposed structure.

EXAMPLE 7

Synthesis of N-{4-[1-(2-Fluoroethyl)-1,2,3,5-(1H)-Tetrazol-4-yl]Phenylmethyl}-N'-[bis(4-Trifluoromethylphenyl)]-Piperazine (Compound 150)

Step A Synthesis of bis(4-trifluoromethylphenyl)methanol as an intermediate

This compound was prepared by a Grignard reaction in which 45.0 grams (0.2 mole) of 4-bromobenzotrifluoride, 5.0 grams (0.22 mole) of magnesium, and 34.8 grams (0.20 mole) of 4-(trifluoromethyl)benzaldehyde were the reagents, and 1000 mL of diethyl ether was the solvent. The yield of bis(4-trifluoromethylphenyl)methanol was 37.0 grams.

Step B Synthesis of bis(4-trifluoromethylphenyl)methyl chloride as an intermediate This compound was prepared in the manner of Step B, Example 1, with 37.0 grams (0.115 mole) of bis(4-trifluoromethylphenyl)methanol, 27.3 grams (0.231 mole) of thionyl chloride, three drops of N,N-dimethylformamide as reagents, and 200 mL of methylene chloride as solvent. The yield of bis(4-trifluoromethylphenyl)methyl chloride was 31.8 grams. The NMR spectrum was consistent with the proposed structure.

Step C Synthesis of N-(ethoxycarbonyl)-N'-[bis(4-trifluoromethyl phenyl)methyl]piperazine as an intermediate This compound was prepared in the manner of Step C, Example 1, with 31.8 grams (0.094 mole) of bis(4-trifluoromethylphenyl)methyl chloride, 15.8 grams (0.1 mole) of ethyl 1-piperazinecarboxylate, 12.9 grams (0.1 mole) of ethyl diisopropylamine, 12.4 grams (0.083 mole) of sodium iodide as reagents, and 250 mL of toluene as solvent. The yield of N-(ethoxycarbonyl)-N'-[bis(4-trifluoromethylphenyl)methyl]piperazine was 17.9 grams. The NMR spectrum was consistent with the proposed structure.

Step D Synthesis of N-[bis(4-trifluoromethylphenyl)methyl] piperazine as an intermediate This compound was prepared in the manner of Step D, Example 1, with 17.9 grams (0.039 mole) of N-(ethoxycarbonyl)-N'-[bis(4-trifluoromethylphenyl) methyl]piperazine, 150 mL of tetrahydrofuran, 25 mL of ethanol, and 50 mL of aqueous 50% sodium hydroxide as reagents. The yield of N-[bis-(4-trifluoromethylphenyl) methyl]piperazine 11.3 grams. The NMR spectrum was consistent with the proposed structure.

Step E Synthesis of 4-(4-methylphenyl)-1,2,3,5-(1 H)-tetrazole as an intermediate A stirred solution of 117 grams (1.0 mole) of 4-cyanotoluene, 65.0 grams (1.0 mole) of sodium azide, and 12.0 grams (0.224 mole) of ammonium chloride 800 mL of N,N-dimethylformamide was heated at 130° C. for three hours. After this time the reaction mixture was cooled and then poured into 800 mL of water and 400 mL of ice. The resulting mixture was acidified to pH 2 with 3N hydrochloric acid, and the resulting solid was collected by filtration. The solid was washed with hexane, triturated with 300 mL of methanol, and dried under reduced pressure to a constant weight, yielding 115 grams of 4-(4-methylphenyl)-1,2,3,5-(1H)-tetrazole. The NMR spectrum was consistent with the proposed structure.

Step F Synthesis of 1-(2-fluoroethyl)-4-(4-methylphenyl)-1, 2,3,5-(1H)-tetrazole as an intermediate Under a nitrogen atmosphere, a stirred solution of 5.0 grams (0.031 mole) 4-(4-methylphenyl)-1,2,3,5-(1H)-tetrazole and 4.8 grams (0.035 mole) of potassium carbonate in 150 mL of acetonitrile was heated to reflux and then cooled to ambient temperature. To this was slowly added 10.0 grams (0.078 mole) of 1-bromo-2-fluoroethane. Upon completion of the addition the reaction mixture was placed in a water bath and cooled to 0° C., where it stirred for one hour. After this time the reaction mixture was heated to reflux, where it stirred for three hours, and then cooled to 0° C., where it stirred for about 18 hours. At the conclusion of this period the reaction mixture was poured into 50 mL of water. The resulting solution was extracted with three 50 mL portions of ethyl acetate. The combined extracts were concentrated under reduced pressure to a residue, which was subjected to column chromatography on silica gel. Elution was accomplished with methylene chloride and acetone. The product-containing fractions were combined and concentrated under reduced pressure, yielding 2.8 grams 1-(2-fluoroethyl)-(4-methylphenyl)-1,2,3,5-(1H)-tetrazole. The NMR spectrum was consistent with the proposed structure.

Step G Synthesis of 4-[1-(2-fluoroethyl)-1,2,3,5-(1H)-tetrazol-4-yl]benzyl bromide as an intermediate Under a light source a stirred solution of 2.8 grams (0.013 mole) of 1-(2-fluoroethyl)-4-(4-methylphenyl)-1,2,3,5-(1H)-tetrazole, 2.4 grams (0.013 mole) of N-bromosuccinimide, and 0.19 gram (0.0008 mole) of benzoyl peroxide in 100 mL of carbon tetrachloride was heated to reflux. Once at reflux the reaction mixture was stirred for five hours. After this time the heat source was removed and the reaction mixture was stirred for about 18 hours. At the conclusion of this period the reaction mixture was filtered, and the filtrate was concentrated under reduced pressure, yielding 0.59 gram of 4-[1-(2-fluoroethyl)-1,2,3,5-(1H)-tetrazol-4-yl]benzyl bromide. The NMR spectrum was consistent with the proposed structure.

Step H Synthesis of N-{4-[1-(2-fluoroethyl)-1,2,3,5-(1H)-tetrazol-4-yl]phenylmethyl}-N'-[bis(4-trifluoromethyl-phenyl)methyl]piperazine (Compound 150)

This compound was prepared in the manner of Example 6, with 0.81 gram (0.002 mole) of N-[bis(4-trifluoromethylphenyl)methyl]piperazine, 0.59 gram (0.002 mole) of 4-[1-(2-fluoroethyl)-1,2,3,5-(1H)-tetrazol-4-yl] benzyl bromide, 0.81 gram (0.006 mole) of N,N-diisopropylethylamine as reagents, and 25 mL of dimethyl sulfoxide as solvent. The yield of N-{4-[1-(2-fluoroethyl)-1,2,3,5-(1H)-tetrazol-4-yl]phenylmethyl}-N'-[bis(4-trifluoromethylphenyl)methyl]piperazine was 0.61 gram. The NMR spectrum was consistent with the proposed structure.

EXAMPLE 8

Synthesis of N-[4-(Pyrid-2-yloxy)Phenylmethyl]-N'-[bis(4-Trifluoromethylphenyl)Methyl]Piperazine (Compound 151)

Step A Synthesis of 4-(pyrid-2-yloxy)benzaldehyde as an intermediate

A stirred mixture of 36.7 grams (0.30 mole) of 4-hydroxybenzaldehyde, 12.9 mL (0.15 mole) of 2-fluoropyridine, and 41.0 grams (0.30 mole) of potassium carbonate, and 1.05 grams of 1,4,7,10,13,16-hexaoxacyclooctadecane in 200 mL of dimethyl sulfoxide was heated at 120° C. for four days. The reaction mixture was cooled to ambient temperature, and 500 mL of water was added. The organic and aqueous layers were separated. The aqueous layer was basified with aqueous 10% sodium hydroxide and extracted with two 400 mL portions of diethyl ether. The ether extracts were combined and washed with one 100 mL portion of aqueous 5% sodium hydroxide, followed by one 100 mL portion of aqueous 10% lithium chloride. The organic layer and extracts were combined, dried with sodium sulfate, and filtered. The filtrate was concentrated under reduced pressure to yield a residue, which was subjected to column chromatography on silica gel. Elution was accomplished with 15–20% acetone in petroleum ether mixtures. The product-containing fractions were combined and concentrated under reduced pressure, yielding 13.5 grams of 4-(pyrid-2-yloxy)benzaldehyde. The NMR spectrum was consistent with the proposed structure.

Step B Synthesis of 4-(pyrid-2-yloxy)benzyl alcohol as an intermediate

This compound was prepared in the manner of Step A, Example 1, with 1.87 grams ( 0.052 mole) of sodium borohydride, 13.5 grams (0.068 moles) of 4-(pyrid-2-yloxy) benzaldehyde as reagents, and 200mL of ethanol as solvent. The yield of 4-(pyrid-2-yloxy)benzyl alcohol was 13.0 grams. The NMR spectrum was consistent with the proposed structure.

Step C Synthesis of 4-(pyrid-2-yloxy)benzyl chloride as an intermediate

This compound was prepared in the manner of Step B, Example 1, with 1.0 mL (0.012 mole) of pyrdine, 4.4 mL (0.06 mole) of thionyl chloride, 8.0 grams (0.04 mole) of 4-(pyrid-2-yloxy)benzyl alcohol as reagents, and 100 mL of anhydrous methylene chloride. The yield of 4-(pyrid-2-yloxy)benzyl chloride was 0.66 grams. The NMR spectrum was consistent with the proposed structure.

Step D Synthesis of N-[4-(pyrid-2-yloxy)phenylmethyl]-N'-[bis(4-trifluoromethylphenyl)methyl]piperazine (Compound 151)

This compound was prepared in the manner of Example 3, with 1.15 grams (0.003 mole) of N-[bis(4-trifluoromethylphenyl)methyl]piperazine, 0.66 gram (0.003 mole) of 4-(pyrid-2-yloxy)benzyl chloride, 1.3 grams (0.01 mole) of N,N-diisopropylethylamine in 10 mL of dimethyl sulfoxide as reagents and 0.1 gram (0.0005 mole) of sodium iodide as catalyst.. The yield of N-[4-(pyrid-2-yloxy) phenylmethyl]-N'-[bis(4-trifluoromethylphenyl)methyl]-piperazine was 0.75 gram. The NMR spectrum was consistent with the proposed structure.

Representative compounds prepared by the methods exemplified above are listed in Table 1. Characterizing properties are given in Table 2.

Biological Data

The N-heterocyclylalkyl- or N-[(polycyclyl)alkyl]-N'-substituted piperazine derivatives of the present invention were incorporated into an artificial diet for evaluation of insecticidal activity against the tobacco budworm (*Heliothis virescens*[Fabricius]) in the following manner. Stock solutions of the test chemical in dimethyl sulfoxide were prepared for each rate of application. One hundred microliters of each of the stock solutions was manually stirred into 50 mL of a molten (65–70° C.) wheat germ-based artificial diet. The 50 mL of molten diet containing the test chemical was poured evenly into twenty wells in the outer four rows of a twenty-five well, five row plastic tray. Each well in the tray was about 1 cm in depth, with an opening of 3 cm by 4 cm at the lip. Molten diet containing only dimethylsulfoxide at the levels used in the test chemical-treated diet was poured into the five wells in the third row of the tray. Each tray therefore contained one test chemical at a single rate of application, together with an untreated control. The rates of application, expressed as the negative log of the molar concentration, and the corresponding concentrations of the stock solution prepared for each rate are shown below:

| Stock Solution | Rate of Application |
|---|---|
| 50 micromolar | 4 |
| 5 | 5 |
| 0.5 | 6 |
| 0.05 | 7 |
| 0.005 | 8 |

Single second instar tobacco budworm larvae were placed in each well. The larvae were selected at a stage of growth at which they uniformly weigh about 5 mg each. Upon completion of infestation, a sheet of clear plastic was heat-sealed over the top of the tray using a common household flat iron. The trays were held at 25° C. at 60% relative humidity for five days in a growth chamber. Lighting was set at 14 hours of light and 10 hours of darkness. After the 5-day exposure period, mortality counts were taken, and the surviving insects were weighed. From the weights of the surviving insects that fed on the treated diet as compared to those insects that fed on the untreated diet, the percent growth inhibition caused by each test chemical was determined.

The compounds of the present invention caused significant inhibition of the growth of the tobacco budworm. The most efficacious compounds were 38, 146, 147, 148, 150, and 151. The data from the diet test are given in Table 3.

Certain N-heterocyclylalkyl- or N-[(polycyclyl)alkyl]-N'-substituted piperazines derivatives causing high growth inhibition in the diet test were also tested for insecticidal activity in foliar evaluations against the tobacco budworm.

In these tests against the tobacco budworm, nine-day-old chick pea plants (*Cicer arietinum*) were sprayed at 20 psi to runoff on both upper and lower leaf surfaces with solutions of test chemical to provide application rates as high as 1000 ppm of test chemical. The solvent used to prepare the solutions of test chemical was 10% acetone or methanol (v/v) and 0.1% of the surfactant octylphenoxypolyethoxyethanol in distilled water. Four replicates, each containing four chick pea plants, for each rate of application of test chemical were sprayed. The treated plants were transferred to a hood, where they were kept until the spray had dried.

The four chick pea plants in each replicate, treated with test chemical as described above, were removed from their pots by cutting the stems just above the soil line. The excised leaves and stems from the four plants in each replicate were placed in individual 8-ounce paper cups, which contained a moistened filter paper. Five second-instar (4–5 days old) tobacco budworms were counted into each cup, taking care not to cause injury. An opaque plastic lid was placed on each cup, which was then held in a growth chamber for a 96 hour exposure period at 25° C. and 50% relative humidity. At the end of the 96 hour exposure period the cups were opened, and the numbers of dead and live insects were counted. Moribund larvae, which were disoriented or unable to crawl normally, were counted as dead. Based on the insect counts the efficacy of the test chemical was expressed in percent control. Percent control is derived from the total number of dead insects (TD) plus the total number of moribund insects (TM) as compared to the total number of insects (TI) in the test:

$$\% \text{ Control} = \frac{TD + TM}{TI} \times 100$$

The condition of the test plants was also observed for phytotoxicity and for reduction of feeding damage as compared to an untreated control.

Of the compounds evaluated in the test on foliage, the most active ones were compounds 147, 150, and 151. Compounds 150 and 151 both provided excellent kills at a low concentration. The data from the foliar tests on the tobacco budworm are given in Table 4. The compounds of the invention were also effective against the cabbage looper and the beet armyworm.

For insecticidal application, the active compounds of the invention are formulated into insecticidal compositions by admixture in insecticidally effective amount with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present insecticidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These insecticidal compositions may be applied either as water-diluted sprays, or dusts, or granules to the areas in which insect control is desired. These formulations may contain as little as 0.1%, 0.2% or 0.5% to as much as 95% or more by weight of active ingredient.

Dusts are free flowing admixtures of the active ingredients with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders are in the form of finely divided particles which disperse readily in water or other dispersant. The wettable powder is ultimately applied to the locus where insect control is desired either as a dry dust or as an emulsion in water or other liquid. Typical carriers for wettable powders include Fuller's earth, kaolin clays, silicas, and other highly absorbent, readily wet, inorganic diluents. Wettable powders normally are prepared to contain about 5–80% of active ingredient, depending on the absorbency of the carrier, and usually also contain a small amount of a wetting, dispersing, or emulsifying agent to facilitate dispersion. For example, a useful wettable powder formulation contains 80.8 parts of the insecticidal compound, 17.9 parts of Palmetto clay, and 1.0 part of sodium lignosulfonate and 0.3 part of sulfonated aliphatic polyester as wetting agents.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isophorone, or other non-volatile organic solvent. For insecticidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing, or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agents, when used, normally comprise from 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as carbon dioxide, propane, or butane, may also be used. Water-soluble or water-dispersible granules are also useful formulations for insecticidal application of the present compounds. Such granular formulations are free-flowing, non-dusty, and readily water-soluble or water-miscible. The soluble or dispersible granular formulations described in U.S. Pat. No. 3,920,442 are useful herein with the present insecticidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active insecticidal compounds of this invention may be formulated and/or applied with other insecticides, fungicides, nematicides, plant growth regulators, fertilizers, or other agricultural chemicals. In using an active compound of this invention, whether formulated alone or with other agricultural chemicals, to control insects, an effective amount and concentration of the active compound is applied to the locus where control is desired. The locus may be, e.g., the insects themselves, plants upon which the insects feed, or the insect habitat. When the locus is the soil, e.g., soil in which agricultural crops have been or will be planted, the composition of the active compound may be applied to and optionally incorporated into the soil. For most applications the effective amount may be as low as, e.g. about 10 to 500 g/ha, preferably about 100 to 250 g/ha.

It is apparent that various modifications may be made in the formulation and application of the compounds of this invention without departing from the inventive concepts herein as defined inventive concepts herein as defined in the claims.

TABLE 1

Insecticidal N-Heterocyclylalkyl- or N-[(Polycyclyl)alkyl]-N'-Substituted-Piperazines

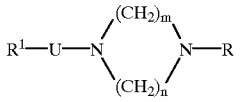

Formula I (FI)

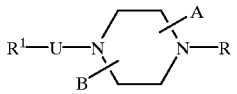

Formula II (FII)

TABLE 1-continued

Insecticidal N-Heterocyclylalkyl- or N-[(Polycyclyl)alkyl]-N'-Substituted-Piperazines

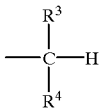

Formula III (FIII)

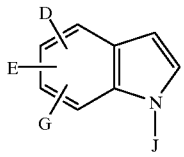

$R^2$

Formula I
U is $CH_2$, J is H, m and n are 2, Ph is phenyl

| Cpd. | R | $R^1$ | $R^3$ | $R^4$ | D | E | G |
|---|---|---|---|---|---|---|---|
| 1 | 2-Cl-Ph | 3-$R^2$ | — | — | 5-Cl | H | H |
| 2 | 4-Cl-Ph | 3-$R^2$ | — | — | 5-Cl | H | H |
| 3 | 3-Cl-Ph | 3-$R^2$ | — | — | 5-Cl | H | H |
| 4 | FIII | 3-$R^2$ | 4-Cl-Ph | Ph | H | H | H |
| 5 | FIII | 3-$R^2$ | 4-Cl-Ph | Ph | 4-Cl | H | H |
| 6 | FIII | 3-$R^2$ | 4-Cl-Ph | Ph | 5-Cl | H | H |
| 7 | FIII | 3-$R^2$ | 4-Cl-Ph | Ph | 6-Cl | H | H |
| 8 | FIII | 3-$R^2$ | 4-Cl-Ph | Ph | 7-Cl | H | H |
| 9 | FIII | 3-$R^2$ | 4-Cl-Ph | Ph | 5-OH | H | H |
| 10 | FIII | 3-$R^2$ | 4-Cl-Ph | Ph | 5-$OCH_3$ | H | H |
| 11 | FIII | 3-$R^2$ | 4-Cl-Ph | Ph | 5-CN | H | H |
| 12 | FIII | 3-$R^2$ | 4-Cl-Ph | Ph | 5-$OCH_3$ | 6-$OCH_3$ | H |
| 13* | FIII | 3-$R^2$ | 4-Cl-Ph | Ph | 4-Cl | H | H |

*J is $CH_3$

Formula I
R is FIII, $R^1$ is 3-$R^2$, U is $CH_2$, J is H, m and n are 2, Ph is phenyl

| Cpd. | $R^3$ | $R^4$ | D | E | G |
|---|---|---|---|---|---|
| 14 | 4-Cl-Ph | Ph | —$O(CH_2)O$— | | H |
| 15 | 4-Cl-Ph | 4-Cl-Ph | H | H | H |
| 16 | 4-Cl-Ph | 4-Cl-Ph | 2-$CH_3$ | H | H |
| 17 | 4-Cl-Ph | 4-Cl-Ph | 4-Cl | H | H |
| 18 | 4-Cl-Ph | 3-Cl-Ph | 4-Cl | H | H |
| 19 | 4-Cl-Ph | 2-Cl-Ph | 4-Cl | H | H |
| 20 | 4-Cl-Ph | 4-Cl-Ph | 4-OH | H | H |
| 21 | 4-Cl-Ph | 4-Cl-Ph | 4-$CH_3$ | H | H |
| 22 | 4-Cl-Ph | 4-Cl-Ph | 4-$NO_2$ | H | H |
| 23 | 4-Cl-Ph | 4-Cl-Ph | 4-CN | H | H |
| 24 | 4-Cl-Ph | 4-Cl-Ph | 4-$CH(CH_3)_2$ | H | H |
| 25 | 4-Cl-Ph | 4-Cl-Ph | 4-$CF_3$ | H | H |
| 26 | 4-Cl-Ph | 4-Cl-Ph | 4-F | H | H |
| 27 | 4-Cl-Ph | 4-Cl-Ph | 5-F | H | H |
| 28 | 4-Cl-Ph | 4-Cl-Ph | 4-$OCH_3$ | H | H |
| 29 | 4-Cl-Ph | 4-Cl-Ph | 5-$OCH_3$ | H | H |
| 30 | 4-Cl-Ph | 4-Cl-Ph | 4-$O(CH_2)_3CH_3$ | H | H |
| 31 | 4-Cl-Ph | 4-Cl-Ph | 4-$OS(O_2)CF_3$ | H | H |
| 32 | 4-Cl-Ph | 4-Cl-Ph | 4-$OC(O)CH_3$ | H | H |
| 33 | 4-Cl-Ph | 4-Cl-Ph | 4-$NHC(O)C_6H_5$ | H | H |
| 34 | 4-Cl-Ph | 4-$OCH_3$-Ph | 4-Cl | H | H |
| 35 | 4-F-Ph | 4-F-Ph | 4-F | H | H |
| 36 | 4-F-Ph | 4-F-Ph | 2-$CH_3$ | H | H |
| 37 | 4-$CH_3$-Ph | 4-$CH_3$-Ph | 4-F | H | H |
| 38 | 4-$OCF_3$-Ph | 4-$OCF_3$-Ph | 4-F | H | H |
| 39 | 4-Cl-Ph | 2,4-$Cl_2$-Ph | 4-Cl | H | H |
| 40 | 4-Cl-Ph | 2,4-$Cl_2$-Ph | 4-F | H | H |
| 41 | 4-Cl-Ph | 3,4-$Cl_2$-Ph | 4-Cl | H | H |
| 42 | 4-Cl-Ph | 3,5-$Cl_2$-Ph | 4-Cl | H | H |
| 43 | 4-Cl-Ph | 4-Cl-Ph | 4-Cl | 5-Cl | H |

Formula I
R is FIII, $R^1$ is 3-$R^2$, U is $CH_2$, J is H, m and n are 2, Ph is phenyl

| Cpd. | $R^3$ | $R^4$ | D | E | G |
|---|---|---|---|---|---|
| 44 | 4-Cl-Ph | 4-Cl-Ph | 4-F | 5-Cl | H |
| 45 | 4-Cl-Ph | 4-Cl-Ph | 4-F | 5-$CH_3$ | H |
| 46 | 4-Cl-Ph | 4-Cl-Ph | 4-$CH_3$ | 5-F | H |

TABLE 1-continued

Insecticidal N-Heterocyclylalkyl- or N-[(Polycyclyl)alkyl]-N'-Substituted-Piperazines

| | | | | | |
|---|---|---|---|---|---|
| 47 | 4-Cl-Ph | 4-Cl-Ph | 4-F | 6-F | H |
| 48 | 4-Cl-Ph | 4-Cl-Ph | 4-F | 6-F | 5-$OCH_3$ |
| 49 | 4-Cl-Ph | 4-Cl-Ph | 4-$OCH_3$ | 5-$OCH_3$ | H |
| 50 | 4-Cl-Ph | 4-Cl-Ph | 4-$C(O)CH_3$ | H | H |
| 51 | 4-Cl-Ph | 4-Cl-Ph | 4-$C(O)OCH(CH_3)_2$ | H | H |

Formula II

R is FIII, $R^1$ is 3-$R^2$, U is CHZ, E, G, and J are H, is H, Ph is phenyl

| Cpd. | $R^3$ | $R^4$ | D | Z | A | B |
|---|---|---|---|---|---|---|
| 52 | 4-Cl-Ph | Ph | H | —$CH_3$ | H | H |
| 53 | 4-Cl-Ph | Ph | 4-$OCH_3$ | —$CH_3$ | H | H |
| 54 | 4-Cl-Ph | Ph | H | —$C_2H_5$ | H | H |
| 55 | 4-Cl-Ph | Ph | 5-$OCH_3$ | —$(CH_2)_2CH_3$ | H | H |
| 56 | 4-Cl-Ph | 4-Cl-Ph | 4-Cl | —$CH_3$ | H | H |
| 57 | 4-Cl-Ph | 4-Cl-Ph | 4-Cl | —$(CH_2)_5CH_3$ | H | H |
| 58 | 4-Cl-Ph | 4-Cl-Ph | 4-Cl | 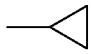 | H | H |
| 59 | 4-Cl-Ph | 4-Cl-Ph | 4-Cl | Ph | H | H |
| 60 | 4-Cl-Ph | 4-Cl-Ph | 4-Cl | H | 2-$CH_3$ | 5-$CH_3$ |

Formula I

R is FIII, $R^1$ is 3-$R^2$, U is $CH_2$, J is H, Ph is phenyl

| Cpd. | $R^3$ | $R^4$ | D | E | G | m | n |
|---|---|---|---|---|---|---|---|
| 61 | 4-Cl-Ph | 4-Cl-Ph | 4-Cl | H | H | 2 | 1 |
| 62 | 4-Cl-Ph | 4-Cl-Ph | 4-Cl | H | H | 3 | 1 |
| 63 | 4-Cl-Ph | 4-Cl-Ph | 4-Cl | H | H | 2 | 3 |

Formula I

U is $CH_2$, J is H, m and n are 2, Ph is phenyl

| Cpd. | R | $R^1$ | $R^3$ | $R^4$ | D | E | G |
|---|---|---|---|---|---|---|---|
| 64 | FIII | 2-$R^2$ | 4-Cl-Ph | 4-Cl-Ph | H | H | H |
| 65 | FIII | 2-$R^2$ | 4-Cl-Ph | 4-Cl-Ph | 5-F | H | H |

Formula I $R^1$ is 3-$R^2$, U is $(CH_2)_2$, D, E, G and J are H, m and n are 2

| Cpd. | R | Cpd. | R |
|---|---|---|---|
| 66 | 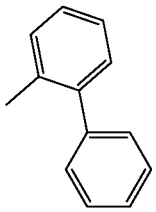 | 68 | 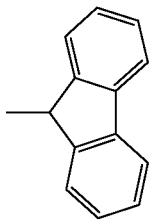 |
| 67 | 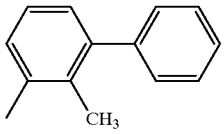 | 69 | 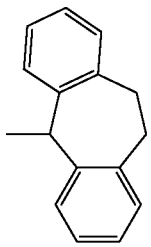 |

Formula I

U is $(CH_2)_2$, J is H, m and n are 2, Ph is phenyl

| Cpd. | R | $R^1$ | $R^3$ | $R^4$ | D | E | G |
|---|---|---|---|---|---|---|---|

TABLE 1-continued

Insecticidal N-Heterocyclylalkyl- or N-[(Polycyclyl)alkyl]-N'-Substituted-Piperazines

| | | | | | | | |
|---|---|---|---|---|---|---|---|
| 70 | FIII | 3-$R^2$ | Ph | Ph | H | H | H |
| 71 | FIII | 3-$R^2$ | Ph | 4-Cl-Ph | H | H | H |
| 72 | FIII | 3-$R^2$ | 4-Cl-Ph | 4-Cl-Ph | H | H | H |
| 73 | FIII | 3-$R^2$ | 4-F-Ph | 4-F-Ph | H | H | H |
| 74 | FIII | 3-$R^2$ | Ph | Ph | 5-F | H | H |
| 75 | FIII | 3-$R^{2*}$ | Ph | 4-Cl-Ph | 5-F | H | H |
| 76 | FIII | 3-$R^2$ | 4-Cl-Ph | Ph | 5-$OCH_3$ | H | H |

*3-$R^2$ has a 1-$CH_3$ sustituent

Formula I

U is $(CH_2)_p$, m and n are 2, Ph is phenyl

| Cpd. | R | $R^1$ | $R^3$ | $R^4$ | p |
|---|---|---|---|---|---|
| 77 | FIII | 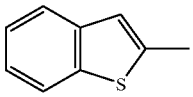 | Ph | 4-Cl-Ph | 1 |
| 78 | FIII | 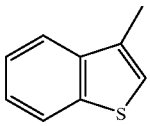 | 4-Cl-Ph | 4-Cl-Ph | 1 |
| 79 | FIII | 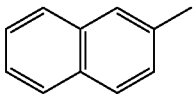 | Ph | 4-Cl-Ph | 1 |
| 80 | FIII | 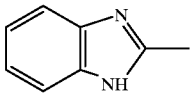 | 4-Cl-Ph | 4-Cl-Ph | 1 |
| 81 | FIII | 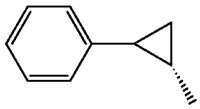 | 4-F-Ph | 4-F-Ph | 1 |
| 82 | FIII | 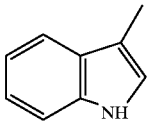 | 4-Cl-Ph | Ph | 3 |

Formula I

U is C═O, J is H, m and n are 2, Ph is phenyl

| Cpd. | R | $R^1$ | $R^3$ | $R^4$ | D | E | G |
|---|---|---|---|---|---|---|---|
| 83 | FIII | 3-$R^2$ | Ph | 4-Cl-Ph | H | H | H |
| 84 | FIII | 3-$R^2$ | 4-Cl-Ph | 4-Cl-Ph | H | H | H |
| 85 | FIII | 2-$R^2$ | 4-Cl-Ph | 4-Cl-Ph | H | H | H |
| 86 | FIII | 2-$R^2$ | 4-Cl-Ph | 4-Cl-Ph | 5-F | H | H |

Formula I

U is $(C{=}O)_p$, m and n are 2, Ph is phenyl

| Cpd. | R | $R^1$ | $R^3$ | $R^4$ | p |
|---|---|---|---|---|---|
| 87 | FIII | 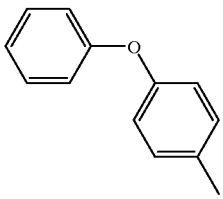 | Ph | H | 1 |

TABLE 1-continued

Insecticidal N-Heterocyclylalkyl- or N-[(Polycyclyl)alkyl]-N'-Substituted-Piperazines

| | | | | | |
|---|---|---|---|---|---|
| 88 | FIII | 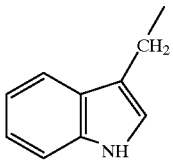 | H | Ph | 1 |
| 89(HCl) | FIII | 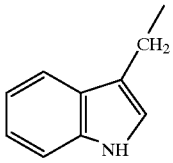 | H | Ph | 1 |
| 90 | FIII | 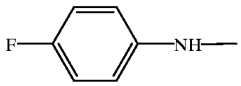 | 4-F-Ph | 4-F-Ph | 1 |
| 91 | FIII | 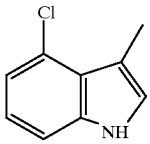 | 4-Cl-Ph | Ph | 2 |

Formula I

U is $(CH_2)_p$, D, E, G, and J are H, m and n are 2, Ph is phenyl

| Cpd. | R | $R^1$ | $R^3$ | $R^4$ | p |
|---|---|---|---|---|---|
| 92 | FIII | 3-$R^2$ | Ph | Ph | 1 |
| 93 | FIII | 3-$R^2$ | 4-F-Ph | Ph | 1 |
| 94 | FIII | 3-$R^2$ | 4-F-Ph | 4-F-Ph | 1 |
| 95 | FIII | 3-$R^2$ | 4-$CH_3$-Ph | 4-$CH_3$-Ph | 3 |
| 96 | FIII | 3-$R^2$ | 4-Cl-Ph | 4-Cl-Ph | 3 |
| 97 | FIII | 3-$R^2$ | 4-F-Ph | 4-F-Ph | 3 |
| 98(HCl) | FIII | 3-$R^2$ | Ph | Ph | 4 |

Formula I

U is $(CH_2)_2$, m and n are 2, Ph is phenyl

| Cpd. | R | $R^1$ | $R^3$ | $R^4$ |
|---|---|---|---|---|
| 99 | FIII | 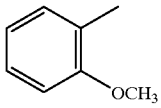 | 4-$OCF_3$-Ph | 4-$OCF_3$-Ph |
| 100 | FIII | 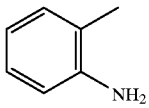 | 4-$OCF_3$-Ph | 4-$OCF_3$-Ph |

Formula I

U is —$CH_2$—CH═CH—, m and n are 2, Ph is phenyl

| Cpd. | R | $R^1$ | $R^3$ | $R^4$ |
|---|---|---|---|---|
| 101 | FIII | Ph | Ph | Ph |
| 102(HCl) | FIII | Ph | 4-F-Ph | 4-F-Ph |
| 103 | FIII | 4-$OCH_3$-Ph | 4-F-Ph | 4-F-Ph |
| 104 | FIII | 4-F-Ph | 4-F-Ph | 4-F-Ph |
| 105 | FIII | 4-Cl-Ph | 4-F-Ph | 4-F-Ph |

TABLE 1-continued
Insecticidal N-Heterocyclylalkyl- or N-[(Polycyclyl)alkyl]-N'-Substituted-Piperazines
| | | | | |
|---|---|---|---|---|
| 106 | FIII | 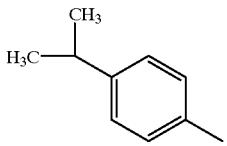 | 4-F-Ph | 4-F-Ph |
| 107 | FIII | 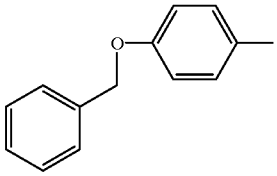 | 4-F-Ph | 4-F-Ph |
| 108 | FIII | 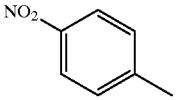 | 4-F-Ph | 4-F-Ph |
Formula I
U is —$CH_2$—CH=CH—, m and n are 2, Ph is phenyl
| Cpd. | R | $R^1$ | $R^3$ | $R^4$ |
|---|---|---|---|---|
| 109 | FIII | 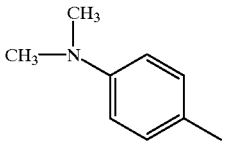 | 4-F-Ph | 4-F-Ph |
| 110 | FIII | 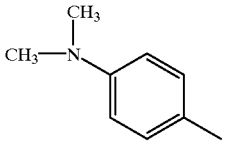 | Ph | Ph |
| 111 | FIII | 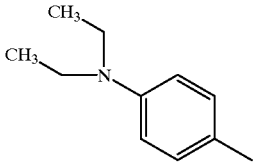 | 4-F-Ph | 4-F-Ph |
Formula I
U is $CH_2$, m and n are 2, Ph is phenyl
| Cpd. | R | $R^1$ | $R^3$ | $R^4$ |
|---|---|---|---|---|
| 112 | FIII | 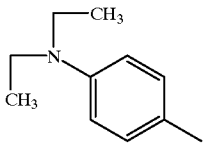 | 4-F-Ph | 4-F-Ph |
| 113 | FIII | 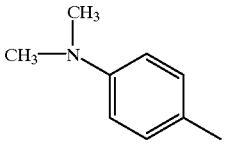 | 4-F-Ph | 4-F-Ph |

TABLE 1-continued
Insecticidal N-Heterocyclylalkyl- or N-[(Polycyclyl)alkyl]-N'-Substituted-Piperazines
| | | | | |
|---|---|---|---|---|
| 114 | FIII | 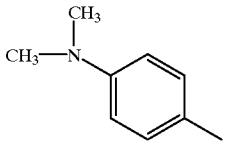 | Ph | Ph |
Formula I
U is —$CH_2$—CH=CH—, m and n are 2, Ph is phenyl
| Cpd. | R | $R^1$ | $R^3$ | $R^4$ |
|---|---|---|---|---|
| 115 | FIII | 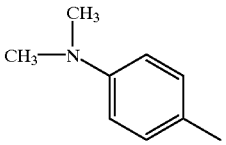 | 4-Cl-Ph | 4-Cl-Ph |
| 116 | FIII | 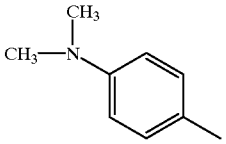 | 4-$OCF_3$-Ph | 4-$OCF_3$-Ph |
| 117 | FIII | 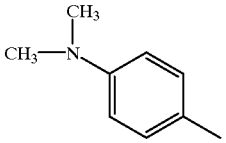 | 4-$CH_3$-Ph | 4-$CH_3$-Ph |
| 118 | FIII | 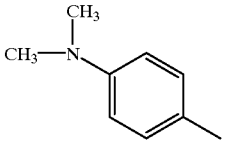 | 4-CN-Ph | 4-CN-Ph |
| 119 | FIII | 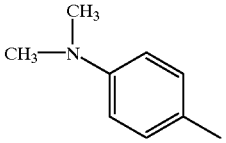 | 4-$OCH_3$-Ph | 4-$OCH_3$-Ph |
Formula I
U is C=O, m and n are 2, Ph is phenyl
| Cpd. | R | $R^1$ | $R^3$ | $R^4$ |
|---|---|---|---|---|
| 120 | FIII | 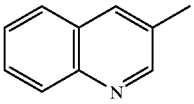 | 4-Cl-Ph | 4-Cl-Ph |
| 121 | FIII | 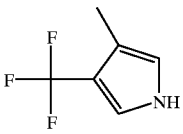 | 4-Cl-Ph | 4-Cl-Ph |

TABLE 1-continued

Insecticidal N-Heterocyclylalkyl- or N-[(Polycyclyl)alkyl]-N'-Substituted-Piperazines

| | | | | |
|---|---|---|---|---|
| 122 | FIII | 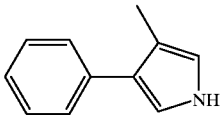 | Ph | 4-Cl-Ph |

Formula I
U is $CH_2$, m and n are 2, Ph is phenyl

| Cpd. | R | $R^1$ | $R^3$ | $R^4$ |
|---|---|---|---|---|
| 123 | FIII | 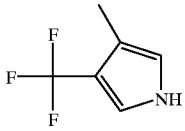 | 4-Cl-Ph | 4-Cl-Ph |
| 124 | FIII | 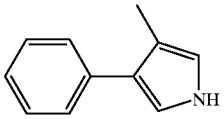 | 4-Cl-Ph | 4-Cl-Ph |

Formula II
U is $CH_2$, A and B are H, Ph is phenyl

| Cpd. | R | $R^1$ | $R^3$ | $R^4$ |
|---|---|---|---|---|
| 125 | FIII | 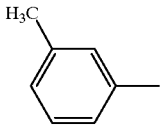 | Ph | Ph |
| 126 | FIII | 3-$C(CH_3)_3$-Ph | Ph | 4-Cl-Ph |
| 127 | FIII | 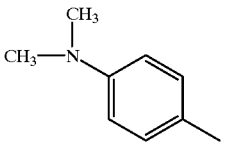 | 2-Cl-Ph | 2-Cl-Ph |
| 128 | FIII | Ph | 4-F-Ph | 4-F-Ph |
| 129 | FIII | 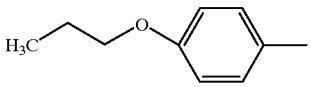 | 4-F-Ph | 4-F-Ph |
| 130 | FIII | 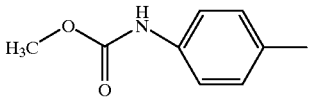 | 4-F-Ph | 4-F-Ph |
| 131 | FIII | 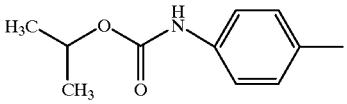 | 4-F-Ph | 4-F-Ph |
| 132 | FIII | 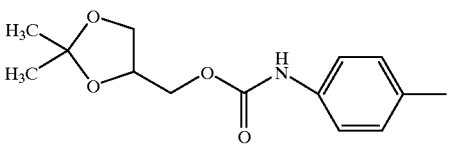 | 4-F-Ph | 4-F-Ph |

TABLE 1-continued
Insecticidal N-Heterocyclylalkyl- or N-[(Polycyclyl)alkyl]-N'-Substituted-Piperazines
| | | | | |
|---|---|---|---|---|
| 133 | FIII | 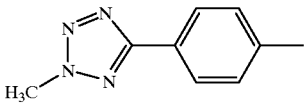 | 4-F-Ph | 4-F-Ph |
| 134 | FIII | 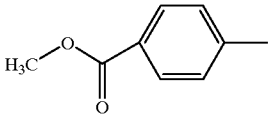 | 4-F-Ph | 4-F-Ph |
| 135 | FIII | 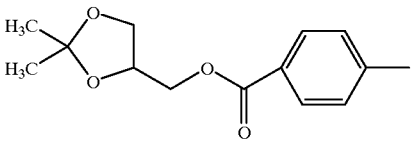 | 4-F-Ph | 4-F-Ph |
| 136 | FIII | 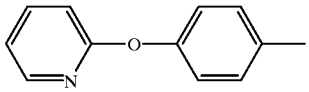 | 4-F-Ph | 4-F-Ph |
| 137 | FIII | 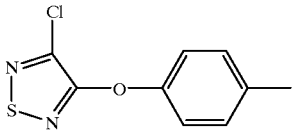 | 4-F-Ph | 4-F-Ph |
| 138 | FIII | 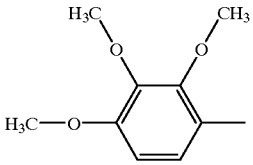 | 4-F-Ph | 4-F-Ph |
| 139 | FIII | 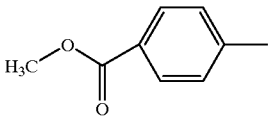 | 4-$CF_3$-Ph | 4-$CF_3$-Ph |
| 140 | FIII | 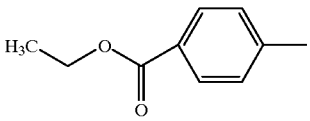 | 4-$CF_3$-Ph | 4-$CF_3$-Ph |
| 141 | FIII | 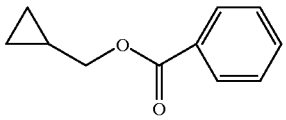 | 4-$CF_3$-Ph | 4-$CF_3$-Ph |
| 142 | FIII | 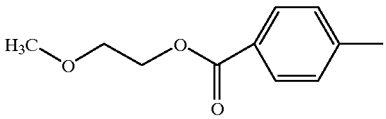 | 4-$CF_3$-Ph | 4-$CF_3$-Ph |

TABLE 1-continued

Insecticidal N-Heterocyclylalkyl- or N-[(Polycyclyl)alkyl]-N'-Substituted-Piperazines

| | | | | |
|---|---|---|---|---|
| 143 | FIII | 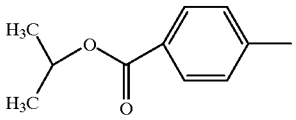 | 4-$CF_3$-Ph | 4-$CF_3$-Ph |
| 144 | FIII | 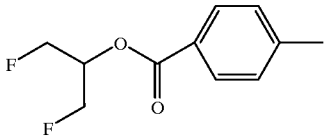 | 4-$CF_3$-Ph | 4-$CF_3$-Ph |
| 145 | FIII | 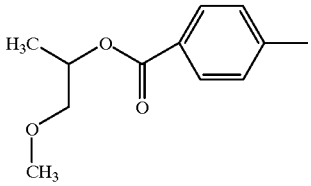 | 4-$CF_3$-Ph | 4-$CF_3$-Ph |
| 146 | FIII | 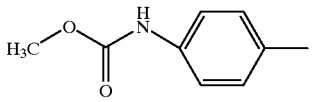 | 4-$CF_3$-Ph | 4-$CF_3$-Ph |
| 147 | FIII | 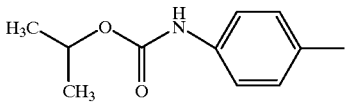 | 4-$CF_3$-Ph | 4-$CF_3$-Ph |
| 148 | FIII | 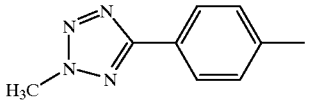 | 4-$CF_3$-Ph | 4-$CF_3$-Ph |
| 149 | FIII | 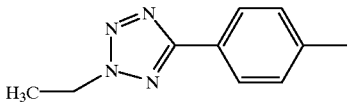 | 4-$CF_3$-Ph | 4-$CF_3$-Ph |
| 150 | FIII | 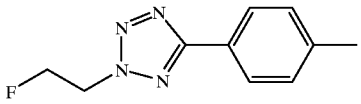 | 4-$CF_3$-Ph | 4-$CF_3$-Ph |
| 151 | FIII | 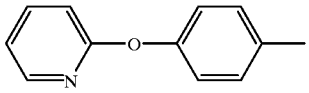 | 4-$CF_3$-Ph | 4-$CF_3$-Ph |
| 152 | FIII | 4-$OCH_3$-Ph | 4-$OCH_3$-Ph | 4-$OCH_3$-Ph |
| 153 (diHCl) | FIII | 4-$OCH_3$-Ph | Ph | Ph |
| 154 (diHCl) | FIII | Ph | Ph | 4-Cl-Ph |
| 155 (diHCl) | FIII | 3-$CH_3$-Ph | Ph | 4-Cl-Ph |
| 156 (diHCl) | FIII | 4-$C(CH_3)_3$-Ph | Ph | 4-Cl-Ph |

TABLE 1-continued
Insecticidal N-Heterocyclylalkyl- or N-[(Polycyclyl)alkyl]-N'-Substituted-Piperazines
| | | | | |
|---|---|---|---|---|
| 157 (diHCl) | FIII | 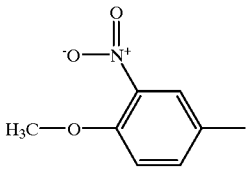 | Ph | 4-Cl-Ph |
| 158 | FIII | 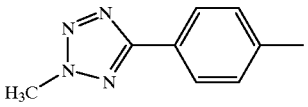 | 4-$OCF_3$-Ph | 4-$OCF_3$-Ph |
| 159 | FIII | 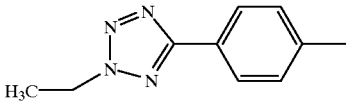 | 4-$OCF_3$-Ph | 4-$OCF_3$-Ph |
| 160 | FIII | 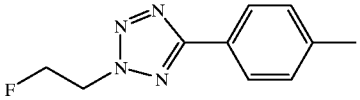 | 4-$OCF_3$-Ph | 4-$OCF_3$-Ph |
| 161 | FIII | 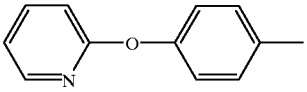 | 4-$OCF_3$-Ph | 4-$OCF_3$-Ph |
| 161 | FIII | 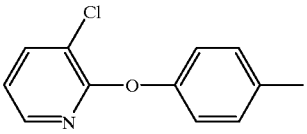 | 4-$OCF_3$-Ph | 4-$OCF_3$-Ph |
| 162 | FIII | 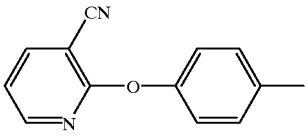 | 4-$OCF_3$-Ph | 4-$OCF_3$-Ph |
| 163 | FIII | 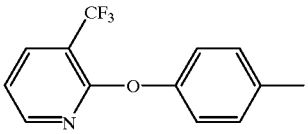 | 4-$OCF_3$-Ph | 4-$OCF_3$-Ph |
| 164 | FIII | 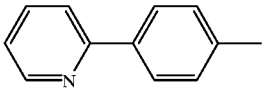 | 4-$OCF_3$-Ph | 4-$OCF_3$-Ph |
| 165 | FIII | 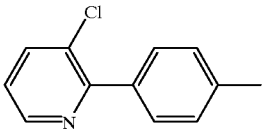 | 4-$OCF_3$-Ph | 4-$OCF_3$-Ph |

TABLE 1-continued
Insecticidal N-Heterocyclylalkyl- or N-[(Polycyclyl)alkyl]-N'-Substituted-Piperazines
| | | | | |
|---|---|---|---|---|
| 166 | FIII | 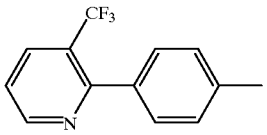 | 4-$OCF_3$-Ph | 4-$OCF_3$-Ph |
| 167 | FIII | 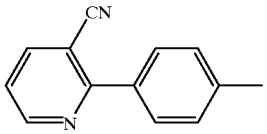 | 4-$OCF_3$-Ph | 4-$OCF_3$-Ph |
| 168 | FIII | 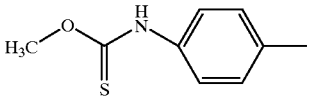 | 4-$OCF_3$-Ph | 4-$OCF_3$-Ph |
| 169 | FIII | 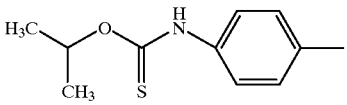 | 4-$OCF_3$-Ph | 4-$OCF_3$-Ph |
| 170 | FIII | 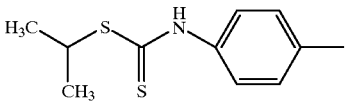 | 4-$OCF_3$-Ph | 4-$OCF_3$-Ph |
| 171 | FIII | 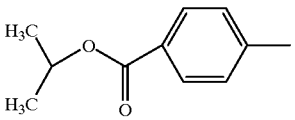 | 4-$OCF_3$-Ph | 4-$OCF_3$-Ph |
| 172 | FIII | 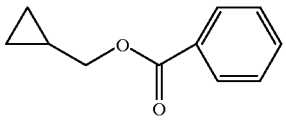 | 4-$OCF_3$-Ph | 4-$OCF_3$-Ph |
| 173 | FIII | 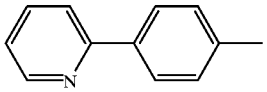 | 4-$CF_3$-Ph | 4-$CF_3$-Ph |
| 174 | FIII | 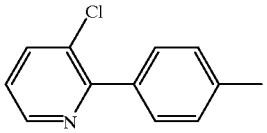 | 4-$CF_3$-Ph | 4-$CF_3$-Ph |
| 175 | FIII | 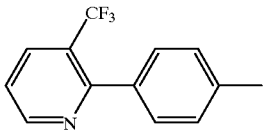 | 4-$CF_3$-Ph | 4-$CF_3$-Ph |
| 176 | FIII | 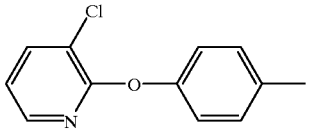 | 4-$CF_3$-Ph | 4-$CF_3$-Ph |

TABLE 1-continued

Insecticidal N-Heterocyclylalkyl- or N-[(Polycyclyl)alkyl]-N'-Substituted-Piperazines

| | | | | |
|---|---|---|---|---|
| 177 | FIII | 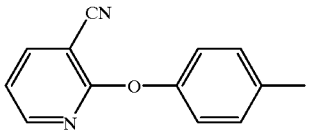 | 4-$CF_3$-Ph | 4-$CF_3$-Ph |
| 178 | FIII | 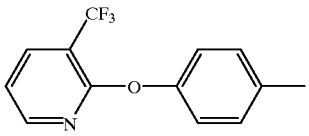 | 4-$CF_3$-Ph | 4-$CF_3$-Ph |
| 179 | FIII | 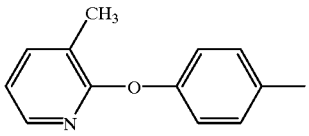 | 4-$CF_3$-Ph | 4-$CF_3$-Ph |
| 180 | FIII | 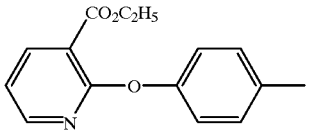 | 4-$CF_3$-Ph | 4-$CF_3$-Ph |
| 181 | FIII | 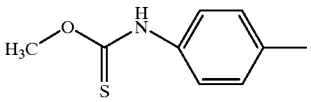 | 4-$CF_3$-Ph | 4-$CF_3$-Ph |
| 182 | FIII | 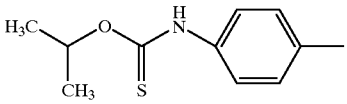 | 4-$CF_3$-Ph | 4-$CF_3$-Ph |
| 183 | FIII | 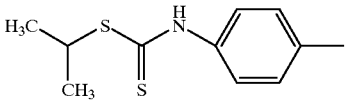 | 4-$CF_3$-Ph | 4-$CF_3$-Ph |

Formula II
U is C═O, A and B are H, Ph is phenyl

| Cpd. | R | $R^1$ | $R^3$ | $R^4$ |
|---|---|---|---|---|
| 184 | FIII | Ph | Ph | Ph |

Formula II
R is FIII, U is $CH_2$, Ph is phenyl

| Cpd. | $R^1$ | $R^3$ | $R^4$ | A | B |
|---|---|---|---|---|---|
| 185 (Isomer 1) | 4-$OCH_3$-Ph | 4-$OCF_3$-Ph | 4-$OCF_3$-Ph | 1-(═O) | 4-(═O) |
| 186 (Isomer 2) | 4-$OCH_3$-Ph | 4-$OCF_3$-Ph | 4-$OCF_3$-Ph | 1-(═O) | 4-(═O) |

TABLE 2

| Cmpd No | Melting Point (° C.) Physical State | Cmpd No | Melting Point (° C.) Physical State |
|---|---|---|---|
| 1 | 62.74 dec | 59 | 100–105 |
| 2 | 72 | 60 | 96–118 |

TABLE 2-continued

| Cmpd No | Melting Point (° C.) Physical State | Cmpd No | Melting Point (° C.) Physical State |
|---|---|---|---|
| 3 | 58, dec @ 68 | 61 | 104–109 |
| 4 | pale oil | 62 | 112–116 |

TABLE 2-continued

| Cmpd No | Melting Point (° C.) Physical State | Cmpd No | Melting Point (° C.) Physical State |
|---|---|---|---|
| 5 | 96–105 | 63 | 75–78 |
| 6 | 78–86 | 64 | foam |
| 7 | 75–85 | 65 | foam |
| 8 | 75–90 | 66 | viscous oil |
| 9 | 115–135 | 67 | soft solid |
| 10 | 72–76 | 68 | 82 dec |
| 11 | oil | 69 | oil |
| 12 | 108 dec | 70 | 62–72 |
| 13 | viscous oil | 71 | 65–76 |
| 14 | oil | 72 | 100–110 dec |
| 15 | 95, 99 dec | 73 | 67–76 |
| 16 | 106–110 | 74 | 146 dec |
| 17 | oil | 75 | 155–180 dec |
| 18 | oil | 76 | 118 dec |
| 19 | oil | 77 | colorless oil |
| 20 | yellow glassy solid | 78 | 84–87 |
| 21 | thick oil | 79 | pale oil |
| 22 | 115 dec | 81 | 164–166 |
| 23 | 121 dec | 82 | 137 dec |
| 24 | 108–113 | 83 | 111 shrinks |
| 25 | white glassy solid | 78 | 84–87 |
| 26 | oil | 85 | 118–121 |
| 27 | 98, 106 dec | 86 | 183–185 |
| 28 | oil | 87 | oil |
| 29 | oil | 88 | 70–79 |
| 30 | oil | 89 | 150–165 |
| 31 | oil | 90 | 193–195 |
| 32 | 105–120 | 91 | 134 shrinks |
| 33 | 125–135 | 92 | solid |
| 34 | 92–100 | 93 | solid |
| 35 | oil | 94 | solid |
| 36 | 65–73 | 95 | solid |
| 37 | oil | 96 | solid |
| 38 | oil | 97 | solid |
| 39 | oil | 98 | solid |
| 49 | 90–108 | 99 | oil |
| 50 | 108–115 | 100 | 92–94 |
| 51 | 94–97 | 101 | solid |
| 52 | oil | 102 | 218–222 |
| 53 | oil | 103 | 83–87 |
| 54 | tan powder mp shrinks at 94 c | 104 | liquid |
| 55 | 80–86 | 105 | liquid |
| 56 | 82–86 | 106 | liquid |
| 57 | 144–149 | 107 | paste |
| 58 | 85–90 | 108 | 63–66 |
| 109 | 140–141 | 133 | liquid |
| 110 | 143–145 | 134 | solid |
| 111 | 93–95 | 135 | oil |
| 112 | oil | 136 | liquid |
| 113 | 92–94 | 137 | solid |
| 114 | 110–113 | 138 | liquid paste |
| 115 | 48–52 | 139 | oil |
| 116 | liquid | 140 | oil |
| 117 | solid | 141 | oil |
| 118 | liquid | 142 | oil |
| 119 | 78–83 | 143 | oil |
| 120 | foam | 144 | oil |
| 121 | foam | 145 | oil |
| 122 | 160–161 | 146 | oil |
| 123 | foam | 147 | oil |
| 124 | foam | 148 | 159–162 |
| 125 | 108–109 | 149 | oil |
| 127 | liquid | 150 | oil |
| 128 | 124–127 c | 151 | liquid |
| 129 | liquid | 152 | oil |
| 130 | liquid | 154 | 221.5–222.2 |
| 131 | liquid | 185 | 152–154 |
| 132 | oil | 186 | 157–159 |

TABLE 3

Insecticidal Activity When Incorporated into the Diet of Tobacco Budworm

| Cmpd. No. | Rate of Application[1] | Percent Growth Inhibition[2,3] |
|---|---|---|
| 1 | 4 | 24 |
| 2 | 4 | 10 |
| 5 | 4 | 90 |
| 6 | 4 | 76 |
| 7 | 4 | 43 |
| 8 | 4 | 44 |
| 10 | 4 | 80 |
| 11 | 4 | 54 |
| 12 | 4 | 28 |
| 13 | 4 | 60 |
| 14 | 4 | 46 |
| 15 | 4 | 94[a] |
| 16 | 4 | 35 |
| 17 | 4 | 98 |
| 18 | 4 | 83 |
| 19 | 4 | 92 |
| 20 | 4 | 18 |
| 21 | 4 | 95[a] |
| 22 | 4 | 96 |
| 23 | 4 | 89[a] |
| 24 | 3.5 | −5 |
| 25 | 4 | 82[a] |
| 26 | 4 | 98[a] |
| 27 | 4 | 98[a] |
| 28 | 4 | 96[a] |
| 29 | 4 | 66 |
| 30 | 4 | 30[a] |
| 31 | 4 | −1 |
| 32 | 4 | 10 |
| 33 | 4 | 15 |
| 34 | 4 | 97[a] |
| 35 | 4 | 90 |
| 37 | 4 | 96 |
| 38 | 4 | 100[a] |
| 39 | 4 | 98[a] |
| 40 | 4 | 99 |
| 41 | 4 | 90 |
| 42 | 4 | 7 |
| 43 | 4 | 95 |
| 44 | 4 | 95 |
| 45 | 4 | 92 |
| 46 | 4 | 96 |
| 47 | 4 | 97 |
| 48 | 4 | 90 |
| 49 | 4 | 82 |
| 50 | 4 | 85[a] |
| 51 | 4 | 25[a] |
| 53 | 4 | 31 |
| 54 | 4 | 64 |
| 55 | 4 | 67 |
| 56 | 4 | 32 |
| 57 | 3.5 | 5 |
| 58 | 4 | 15 |
| 59 | 4 | 4 |
| 60 | 4 | 77 |
| 61 | 4 | 26 |
| 62 | 4 | 29 |
| 63 | 4 | 81 |
| 64 | 4 | 21 |
| 65 | 4 | 5 |
| 67 | 4 | 31 |
| 72 | 4 | 62[a] |
| 73 | 4 | 36 |
| 74 | 4 | −6 |
| 75 | 4 | 2 |
| 76 | 4 | 38 |
| 78 | .35 | −7 |
| 80 | 4 | 86 |
| 81 | 4 | 10 |
| 82 | 4 | 14 |
| 84 | 3.5 | 16 |
| 85 | 4 | 1 |
| 86 | 4 | 1 |

TABLE 3-continued

| Insecticidal Activity When Incorporated into the Diet of Tobacco Budworm | | |
|---|---|---|
| Cmpd. No. | Rate of Application[1] | Percent Growth Inhibition[2,3] |
| 90 | 4 | −3 |
| 91 | 4 | 9 |
| 99 | 3.5 | 100 |
| 100 | 4 | 63 |
| 101 | 4 | 7[a] |
| 102 | 4 | 35[b] |
| 114 | 4 | 26 |
| 115 | 4 | 54 |
| 116 | 4 | 100[b] |
| 117 | 4 | 9 |
| 118 | 3.5 | 13 |
| 119 | 3.5 | 3 |
| 122 | 4 | 11 |
| 123 | 4 | 54[a] |
| 124 | 4 | 9 |
| 129 | 4 | 38 |
| 130 | 4 | 78 |
| 131 | 4 | 89 |
| 133 | 4 | 48 |
| 136 | 4 | 87 |
| 138 | 4 | 9 |
| 139 | 4 | 33 |
| 140 | 4 | 94 |
| 141 | 4 | 100 |
| 142 | 4 | 90 |
| 143 | 4 | 77 |
| 144 | 4 | 43 |
| 145 | 4 | 99 |
| 146 | 4 | 100 |
| 147 | 4 | 100 |
| 148 | 4 | 98 |
| 149 | 4 | 100 |
| 150 | 4 | 100 |
| 151 | 4 | 100 |
| 152 | 4 | 98[a] |
| 182 | 4 | 92 |
| 186 | 4 | 40 |

TABLE 4

| Insecticidal Activity When Applied as Foliar Sprays | | |
|---|---|---|
| Cmpd No. | Rate of Application (ppm) | Percent Control[1] TBW |
| 4 | 1000 | 0 |
| 6 | 300 | 0 |
| 17 | 300 | 62[a] |
| 26 | 300 | 60 |
| 38 | 300 | 100[a] |
| 39 | 300 | 95 |
| 147 | 300 | 100 |
| 150 | 100 | 95 |
| 151 | 100 | 90 |
| 152 | 1000 | 40 |

[a] = average of two tests

[1]Percent control is derived from the total number of dead insects (TD) plus the total number of moribund insects (TM) as compared to the total number of insects (TI) used in the test, $$\% \text{ Control} = \frac{TD + TM}{TI} \times 100$$

What is claimed is:

1. A compound of the formula

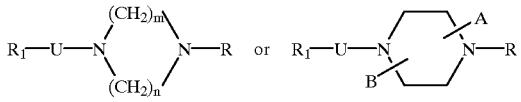

in which:

A and B are independently selected from lower alkyl;

U is selected from lower alkylidene, lower alkenylidene, and CH—Z, where Z is independently selected from hydrogen, lower alkyl, lower cycloalkyl, and phenyl;

R is

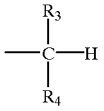

where $R^3$ and $R^4$ are independently selected from phenyl, optionally substituted with, halogen, lower alkyl, lower haloalkyl, lower alkoxy, lower haloalkoxy, lower alkenyl, or phenyl;

$R^1$ is phenyl, naphthyl, tetrazolylphenyl, phenylcyclopropyl, phenoxyphenyl, benzyloxyphenyl, pyridylphenyl, pyridyloxyphenyl, or thiadiazolyloxyphenyl, each optionally substituted with halogen, cyano, hydroxy, lower alkyl, lower haloalkyl, lower alkoxy, amino, lower dialkylamino, nitro, lower haloalkylsulfonyloxy, lower alkylcarbonyloxy, lower alkylcarbonylamino, lower alkoxycarbonyl, lower alkoxyalkoxycarbonyl, lower cycloalkylalkoxycarbonyl, lower alkoxyalkylalkoxycarbonyl, lower alkoxycarbonylamino, alkoxythiocarbonylamino, lower alkyldithiocarbonylamino, lower dialkyldioxolylalkoxycarbonylamino, or halophenylamino; or lower alkyl substituted with any one of the foregoing cyclic $R^1$ groups;

m is 2 or 3 and n is 1, 2, or 3;

halogen is chlorine, fluorine, or bromine, lower means having from 1 to 6 carbon atoms, and any aliphatic chain of three or more carbons may be straight or branched.

2. A compound of claim 1 in which

U is selected from lower alkylidene, carbonyl, lower alkenylidene, and CH—Z, where Z is independently selected from hydrogen and lower alkyl;

R is and

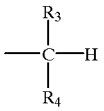

where $R^3$ and $R^4$ are independently selected from hydrogen and phenyl, optionally substituted with halogen, lower alkyl, lower haloalkyl, lower alkoxy, lower haloalkoxy;

$R^1$ is phenyl, tetrazolylphenyl, pyridylphenyl, pyridyloxyphenyl; each optionally substituted with halogen, cyano, hydroxy, lower alkyl, lower haloalkyl, lower alkoxy, amino, lower dialkylamino, lower alkylcarbonyloxy, lower alkylcarbonylamino, lower alkoxycarbonyl, lower alkoxyalkoxycarbonyl, lower cycloalkylalkoxycarbonyl, lower alkoxyalkylalkoxycarbonyl, or lower alkoxycarbonylamino; or lower alkyl substituted with any one of the foregoing cyclic $R^1$ groups;

m and n are 2; and halogen is chlorine or fluorine, for aliphatic groups lower means having from 1 to 3 carbon atoms, and for alicyclic groups lower means having 3 to 6 carbons.

3. A compound of claim 2 of the formula

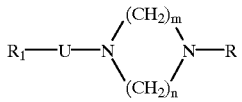

in which

R is

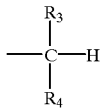

where $R^3$ and $R^4$ are independently selected from phenyl substituted in the 4-position with halogen, lower alkyl, lower haloalkyl, lower alkoxy, or lower haloalkoxy;

$R^1$ is phenyl substituted in the 4-position with lower dialkylamino, lower alkoxycarbonylamino, tetrazolyl, pyridyl, or pyridyloxy; each tetrazolyl or pyridyl group optionally substituted with halogen, cyano, lower alkyl, lower haloalkyl, or lower alkoxy;

m and n are 2; and halogen is chlorine or fluorine, for aliphatic groups lower means having from 1 to 3 carbon atoms, and for alicyclic groups lower means having 3 to 6 carbons.

4. A compound of claim 3 in which U is $CH_2$, and $R^3$ and $R^4$ are independently selected from chlorophenyl, fluorophenyl, methylphenyl, trifluoromethylphenyl, methoxyphenyl, and trifluoromethoxyphenyl.

5. A composition of claim 3 in which

R is

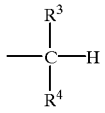

where $R^3$ and $R^4$ are independently selected from 4-chlorophenyl, 4-fluorophenyl, 4-methylphenyl, 4-trifluoromethylphenyl, 4-methoxyphenyl, and 4-trifluoromethoxyphenyl;

$R^1$ is 3-$R^2$, where $R^2$ is

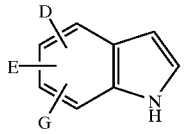

where D is selected from hydrogen, hydroxy, chloro, fluoro; methyl, phenylcarbonylamino, and methoxy, and E and G are independently selected from hydrogen, chloro, fluoro; methyl, and methoxy.

6. A composition of claim 5 in which $R^2$ is

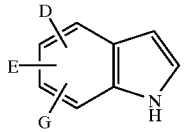

in which D is selected from hydrogen, 4-chloro, 4-fluoro, 4-hydroxy, and 4-phenylcarbonylamino; E is selected from hydrogen, 5-chloro, 5-methyl, 6-fluoro; G is selected from hydrogen and 5-methoxy; and $R^3$ and $R^4$ are independently selected from 4-chlorophenyl, 4-fluorophenyl, 4-methylphenyl, 4-trifluoromethylphenyl, and 4-trifluoromethoxyphenyl.

7. A composition of claim 6 in which $R^3$ and $R^4$ are each 4-trifluoromethoxyphenyl.

8. A composition of claim 6 in which E and G are hydrogen.

9. A composition of claim 8 in which D is 4-fluoro.

10. The composition of claim 9 in which $R^3$ and $R^4$ are each 4-trifluoromethoxyphenyl.

11. The composition of claim 9 in which $R^3$ and $R^4$ are each 4-chlorophenyl.

12. The composition of claim 9 in which $R^3$ and $R^4$ are each 4-fluorophenyl.

13. The composition of claim 9 in which $R^3$ and $R^4$ are each 4-methylphenyl.

14. A composition of claim 6 in which and $R^3$ and $R^4$ are each 4-chlorophenyl.

15. A composition of claim 14 in which D is 4-fluoro.

16. The composition of claim 15 in which E is 5-chloro, and G is hydrogen.

17. The composition of claim 15 in which E is 5-methyl, and G is hydrogen.

18. The composition of claim 15 in which E is 6-fluoro, and G is hydrogen.

19. The composition of claim 15 in which E is 6-fluoro, and G is 5-methoxy.

20. A composition of claim 14 in which E and G are hydrogen.

21. The composition of claim 20 in which D is 4-hydroxy.

22. The composition of claim 20 in which D is 4-phenylcarbonylamino.

23. A compound of claim 4 in which

R is

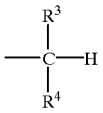

where $R^3$ and $R^4$ are independently selected from 4-chlorophenyl, 4-fluorophenyl, 4-methylphenyl, 4-trifluoromethylphenyl, 4-methoxyphenyl, and 4-trifluoromethoxyphenyl;

$R^1$ is phenyl substituted in the 4-position with lower dialkylamino, lower alkoxycarbonylamino, tetrazolyl, pyridyl, or pyridyloxy; each tetrazolyl or pyridyl group optionally substituted with halogen, cyano, lower alkyl, lower haloalkyl, or lower alkoxy, with the proviso that when $R^1$ is lower dialkylaminophenyl, $R^3$ and $R^4$ are each trifluoromethoxyphenyl.

24. A compound of claim 23 in which $R^1$ is lower dialkylaminophenyl.

25. The compound of claim 24 in which $R^1$ is dimethylaminophenyl.

26. A compound of claim 23 in which $R^1$ is phenyl substituted in the 4-position with lower alkoxycarbonylamino, tetrazol-4-yl or pyrid-2-yloxy; each tetrazolyl or pyridyl group optionally substituted with lower alkyl, lower haloalkyl, or lower alkoxy; and $R^3$ and $R^4$ are independently selected from 4-trifluoromethylphenyl and 4-trifluoromethoxyphenyl.

27. A compound of claim 26 in which $R^3$ and $R^4$ are each 4-trifluoromethylphenyl.

28. The compound of claim 27 in which $R^1$ is N-4-(methoxycarbonylamino)phenyl.

29. The compound of claim 27 in which $R^1$ is N-4-(1-methylethoxycarbonylamino)phenyl.

30. The compound of claim 27 in which $R^1$ is N-4-(1-methyl-1,2,3,5-(1-H)-tetrazol4-yl)phenyl.

31. The compound of claim 27 in which $R^1$ is N-4-[1-(2-fluorooethyl)-1,2,3,5-(1-H)-tetrazol-4-yl]phenyl.

32. The compound of claim 27 in which $R^1$ is N-4-(pyrid-2-yloxy)phenyl.

33. The compound N-[bis(4-trifluoromethoxyphenyl) methyl]piperazine.

34. An insecticidal composition comprising an insecticidally effective amount of an adjuvant or carrier and at least one compound of the formula

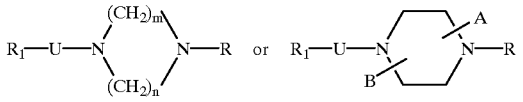

in which:

A and B are independently selected from lower alkyl;

U is selected from lower alkylidine, lower alkenylidene, and CH—Z, where Z is independently selected from hydrogen, lower alkyl, lower cycloalkyl, and phenyl;

R is selected from phenyl, optionally substituted with halogen, lower alkyl, lower alkoxy, phenyl, or phenoxy, and from a dibenzocyclo($C_{5-8}$)alkyl, optionally substituted with halogen, lower alkyl, or lower alkoxy; and

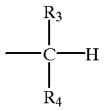

where $R_3$ and $R_4$ are independently selected from phenyl, optionally substituted with, halogen, lower alkyl, lower haloalkyl, lower alkoxy, lower haloalkoxy, lower alkenyl, or phenyl;

$R_1$ is phenyl, naphthyl, tetrazolylphenyl, phenylcyclopropyl, phenoxyphenyl, benzyloxyphenyl, pyridylphenyl, pyridyloxyphenyl, thiadiazolyloxyphenyl, benzothienyl, benzimidazolyl, indolyl, pyrrolyl, or quinolyl, each optionally substituted with halogen, cyano, hydroxy, lower alkyl, lower haloalkyl, lower alkoxy, amino, lower dialkylamino, nitro, lower haloalkylsulfonyloxy, lower alkoxycarbonyl, lower alkoxyalkoxycarbonyl, lower cycloalkylalkoxycarbonyl, lower alkoxyalkylalkoxycarbonyl, lower alkoxycarbonylamino, alkoxythiocarbonylamino, lower alkyldithiocarbonylamino, lower dialkyldioxolylalkoxycarbonylamino, or halophenylamino; or lower alkyl substituted with any one of the foregoing cyclic $R_1$ groups; or 3-$R_2$, where $R_2$ is

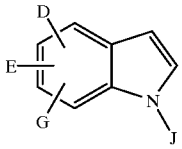

where D, E, and G are independently selected from hydrogen, hydroxy, halogen, cyano, lower alkyl, lower haloalkyl, lower alkoxy, nitro, lower haloalkylsulfonyloxy, lower alkylcarboxylato, lower alkylcarbonylamino, arylcarbonylamino, lower alkylcarbonyl. lower alkoxycarbonyl, or D and E taken together form the group —O(CH2)O—, and J is hydrogen or lower alkyl;

m is 2or 3 and n is 1, 2, or 3;

halogen is chlorine, fluorine, or bromine, lower means having from 1 to 6 carbon atoms, and any aliphatic chain of three or more carbons may be straight or branched.

35. A composition of claim 34 in which

U is selected from lower alkylidene, carbonyl, lower alkenylidene, and CH—Z, where Z is independently selected from hydrogen and lower alkyl;

R is selected from phenyl, optionally substituted with halogen, lower alkyl, lower alkoxy, phenyl, or phenoxy; and

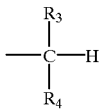

where $R^3$ and $R^4$ are independently selected from hydrogen and phenyl, optionally substituted with halogen, lower alkyl, lower haloalkyl, lower alkoxy, lower haloalkoxy;

$R^1$ is phenyl, tetrazolylphenyl, pyridylphenyl, pyridyloxyphenyl; each optionally substituted with halogen, cyano, hydroxy, lower alkyl, lower haloalkyl, lower alkoxy, amino, lower dialkylamino, lower alkylcarbonyloxy, lower alkylcarbonylamino, lower alkoxycarbonyl, lower alkoxyalkoxycarbonyl, lower cycloalkylalkoxycarbonyl, lower alkoxyalkylalkoxycarbonyl, or lower alkoxycarbonylamino; or lower alkyl substituted with any one of the foregoing cyclic $R^1$groups; or 3-$R^2$, where $R^2$ is

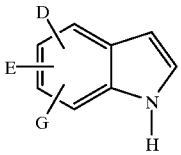

where D is hydrogen, hydroxy, chloro, fluoro; methyl, methoxy, or phenylcarbonylamino; E and G are independently selected from hydrogen, chloro, fluoro; methyl, and methoxy, with the proviso that when $R^1$ is lower dialkylaminophenyl, $R^3$ and $R^4$ are each trifluoromethoxyphenyl;

m and n are 2; and halogen is chlorine or fluorine, for aliphatic groups lower means having from 1 to 3 carbon atoms, and for alicyclic groups lower means having 3 to 6 carbons.

36. A composition of claim 35 wherein said compound is of the formula

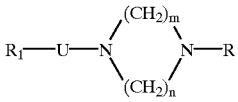

in which

R is

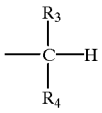

where $R^3$ and $R^4$ are independently selected from phenyl substituted in the 4-position with halogen, lower alkyl, lower haloalkyl, lower alkoxy, or lower haloalkoxy;

$R^1$ is phenyl substituted in the 4-position with lower dialkylamino, lower alkoxycarbonylamino, tetrazolyl, pyridyl, or pyridyloxy; each tetrazolyl or pyridyl group optionally substituted with halogen, cyano, lower alkyl, lower haloalkyl, or lower alkoxy; or 3-$R^2$, where $R^2$ is

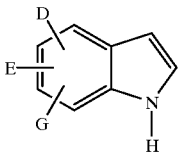

where D is hydrogen, 4-chloro, 4-fluoro, 4-hydroxy, or 4-phenylcarbonylamino; E is hydrogen, 5-chloro, 5-methyl, or 6-fluoro; G is hydrogen or 5-methoxy;

m and n are 2; and halogen is chlorine or fluorine, for aliphatic groups lower means having from 1 to 3 carbon atoms, and for alicyclic groups lower means having 3 to 6 carbons.

37. A composition of claim 36 in which U is $CH_2$, and $R^3$ and $R^4$ are independently selected from chlorophenyl, fluorophenyl, methylphenyl, trifluoromethylphenyl, methoxyphenyl, and trifluoromethoxyphenyl.

38. A composition of claim 37 in which

R is

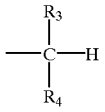

where $R^3$ and $R^4$ are independently selected from 4-chlorophenyl, 4-fluorophenyl, 4-methylphenyl, 4-trifluoromethylphenyl, 4-methoxyphenyl, and 4-trifluoromethoxyphenyl;

$R^1$ is phenyl substituted in the 4-position with lower dialkylamino, lower alkoxycarbonylamino, tetrazolyl, pyridyl, or pyridyloxy; each tetrazolyl or pyridyl group optionally substituted with halogen, cyano, lower alkyl, lower haloalkyl, or lower alkoxy, with the proviso that when $R^1$ is lower dialkylaminophenyl, $R^3$ and $R^4$ are each trifluoromethoxyphenyl.

39. A composition of claim 38 in which $R^1$ is lower dialkylaminophenyl.

40. The composition of claim 39 in which $R^1$ is dimethylaminophenyl.

41. A composition of claim 38 in which $R^1$ is phenyl substituted in the 4-position with lower alkoxycarbonylamino, tetrazol-4-yl or pyrid-2-yloxy; each tetrazolyl or pyridyl group optionally substituted with lower alkyl, lower haloalkyl, or lower alkoxy; and $R^3$ and $R^4$ are independently selected from 4-trifluoromethylphenyl and 4-trifluoromethoxyphenyl.

42. A composition of claim 41 in which $R^3$ and $R^4$ are each 4-trifluoromethylphenyl.

43. The composition of claim 42 in which $R^1$ is N-4-(methoxycarbonylamino)phenyl.

44. The composition of claim 42 in which $R^1$ is N-4-(1-methylethoxycarbonylamino)phenyl.

45. The composition of claim 42 in which $R^1$ is N-4-(1-methyl-1,2,3,5-(1-H)-tetrazol-4-yl)phenyl.

46. The composition of claim 42 in which $R^1$ is N-4-[1-(2-fluorooethyl)-1,2,3,5-(1-H)-tetrazol-4-yl]phenyl.

47. The composition of claim 42 in which $R^1$ is N-4-(pyrid-2-yloxy)phenyl.

48. The composition of claim 34 in which said compound is N-[bis(4-trifluoromethoxyphenyl)methyl]piperazine.

49. A method for controlling insects, comprising the steps of identifying a locus where insect control is needed and applying to said locus at least one compound of the formula

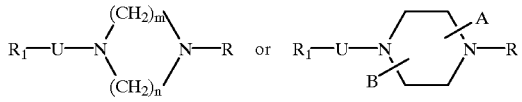

in which:

A and B are independently selected from lower alkyl;

U is selected from lower alkylidine, lower alkenylidene, and CH—Z, where Z is independently selected from hydrogen, lower alkyl, lower cycloalkyl, and phenyl;

R is selected from phenyl, optionally substituted with halogen, lower alkyl, lower alkoxy, phenyl, or phenoxy, and from a dibenzocyclo($C_{5-8}$)alkyl, optionally substituted with halogen, lower alkyl, or lower alkoxy; and

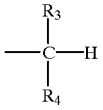

where $R_3$ and $R_4$ are independently selected from phenyl, optionally substituted with, halogen, lower alkyl, lower haloalkyl, lower alkoxy, lower haloalkoxy, lower alkenyl, or phenyl;

$R_1$ is phenyl, naphthyl, tetrazolylphenyl, phenylcyclopropyl, phenoxyphenyl, benzyloxyphenyl, pyridylphenyl, pyridyloxyphenyl, thiadiazolyloxyphenyl, benzothienyl, benzimidazolyl, indolyl, pyrrolyl, or quinolyl, each optionally substituted with halogen, cyano, hydroxy, lower alkyl, lower haloalkyl, lower alkoxy, amino, lower dialkylamino, nitro, lower haloalkylsulfonyloxy, lower alkoxycarbonyl, lower alkoxyalkoxycarbonyl, lower cycloalkylalkoxycarbonyl, lower alkoxyalkylalkoxycarbonyl, lower alkoxycarbonylamino, alkoxythiocarbonylamino, lower alkyldithiocarbonylamino, lower dialkyldioxolylalkoxycarbonylamino, or halophenylamino; or lower alkyl substituted with any one of the foregoing cyclic $R_1$ groups; or 3-$R_2$, where $R_2$ is

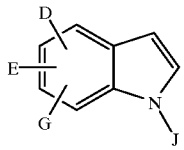

where D, E, and G are independently selected from hydrogen, hydroxy, halogen, cyano, lower alkyl, lower haloalkyl, lower alkoxy, nitro, lower haloalkylsulfonyloxy, lower alkylcarboxylato, lower alkylcarbonylamino, arylcarbonylamino, lower alkylcarbonyl. lower alkoxycarbonyl, or D and E taken together form the group —O(CH2)O—, and J is hydrogen or lower alkyl;

m is 2 or 3 and n is 1, 2, or 3;

halogen is chlorine, fluorine, or bromine, lower means having from 1 to 6 carbon atoms, and any aliphatic chain of three or more carbons may be straight or branched.

* * * * *